United States Patent
Messina

(10) Patent No.: US 9,271,486 B2
(45) Date of Patent: Mar. 1, 2016

(54) COMBINATION ANIMAL REPELLENTS

(71) Applicant: James J. Messina, Long Valley, NJ (US)

(72) Inventor: James J. Messina, Long Valley, NJ (US)

(73) Assignee: James J. Messina, Long Valley, NJ (US)

( * ) Notice: Subject to any disclaimer, the term of this patent is extended or adjusted under 35 U.S.C. 154(b) by 0 days.

(21) Appl. No.: 14/834,583

(22) Filed: Aug. 25, 2015

(65) Prior Publication Data

US 2015/0359230 A1     Dec. 17, 2015

Related U.S. Application Data

(63) Continuation-in-part of application No. 14/356,988, filed as application No. PCT/US2012/061817 on Oct. 25, 2012.

(60) Provisional application No. 61/557,985, filed on Nov. 10, 2011, provisional application No. 61/638,590, filed on Apr. 26, 2012.

(51) Int. Cl.
*A01K 29/00* (2006.01)
*A01C 1/06* (2006.01)
*A01N 25/00* (2006.01)

(52) U.S. Cl.
CPC .. *A01N 25/00* (2013.01); *A01C 1/06* (2013.01)

(58) Field of Classification Search
CPC ....... A01N 49/00; A01N 65/00; A01N 27/00; A01N 25/26; A01G 7/06; A01M 29/12
USPC .................. 119/712; 424/405, 406, 412, 725; 47/57.6
See application file for complete search history.

(56) References Cited

U.S. PATENT DOCUMENTS

| | | |
|---|---|---|
| 3,980,773 A | 9/1976 | Oh |
| 4,058,067 A | 11/1977 | Wright |
| 4,169,902 A | 10/1979 | De Long |
| 4,172,557 A | 10/1979 | Davis |
| 4,388,303 A | 6/1983 | Allan |
| 4,455,304 A | 6/1984 | Yaralian |
| 4,536,583 A | 8/1985 | Mookherjee et al. |
| 4,614,299 A | 9/1986 | Van Loveren et al. |
| 4,666,767 A | 5/1987 | Von Kohorn |
| 4,668,294 A | 5/1987 | Harding, Jr. |
| 4,735,803 A | 4/1988 | Katz |
| 4,783,335 A | 11/1988 | Lipshitz |
| 4,821,452 A | 4/1989 | Beckley |
| 4,849,006 A | 7/1989 | Knudson, Jr. |
| 4,965,070 A | 10/1990 | Messina |
| 4,971,796 A | 11/1990 | Sjogren |
| 4,983,390 A | 1/1991 | Levy |
| 5,017,377 A | 5/1991 | Sikinami et al. |
| 5,183,661 A | 2/1993 | Messina |
| 5,368,866 A | 11/1994 | Loucas |
| 5,679,129 A | 10/1997 | Hon |
| 5,716,602 A | 2/1998 | Uick |
| 5,738,851 A | 4/1998 | Colavito |
| 5,783,204 A | 7/1998 | Messina |
| 5,858,384 A | 1/1999 | Levy |
| 5,885,605 A | 3/1999 | Levy |
| 5,896,692 A | 4/1999 | Collora et al. |
| 5,902,596 A | 5/1999 | Levy |
| 6,001,874 A | 12/1999 | Veierov |
| 6,004,572 A | 12/1999 | Harvan et al. |
| 6,036,971 A | 3/2000 | Kimoto et al. |
| 6,057,266 A | 5/2000 | Colvin |
| 6,083,621 A | 7/2000 | Sugimoto |
| 6,110,463 A | 8/2000 | Riggs et al. |
| 6,117,428 A | 9/2000 | Jarrett |
| 6,192,621 B1 | 2/2001 | Fain |
| 6,199,000 B1 | 3/2001 | Keller et al. |
| 6,221,649 B1 | 4/2001 | Malvar et al. |
| 6,254,880 B1 | 7/2001 | Messina |
| 6,266,917 B1 | 7/2001 | Hight |
| 6,299,663 B1 | 10/2001 | Phinney |
| 6,331,193 B1 | 12/2001 | Phinney |
| 6,337,081 B1 | 1/2002 | Warberg |
| 6,372,240 B1 | 4/2002 | Messina |
| 6,383,508 B1 | 5/2002 | Messina |
| 6,391,336 B1 | 5/2002 | Royer |
| 6,491,949 B2 | 12/2002 | Faour et al. |
| 6,500,463 B1 | 12/2002 | Van Lengerich |
| 6,548,085 B1 | 4/2003 | Zobitne et al. |
| 6,635,266 B2 | 10/2003 | Messina |
| 6,641,830 B1 | 11/2003 | Markham |
| 6,645,516 B2 | 11/2003 | Auberger et al. |
| 6,652,870 B2 | 11/2003 | Campbell et al. |
| 6,793,937 B2 | 9/2004 | Quong |
| 6,849,614 B1 | 2/2005 | Bessette et al. |
| 6,852,328 B1 | 2/2005 | Voris et al. |
| 6,887,828 B2 | 5/2005 | Allen et al. |

(Continued)

FOREIGN PATENT DOCUMENTS

| | | |
|---|---|---|
| EP | 0724826 B1 | 4/2000 |
| WO | 9102534 A1 | 3/1991 |

(Continued)

OTHER PUBLICATIONS

International Search Report dated Jan. 25, 2013 for International Application No. PCT/US2012/061817, entitled "Combination Animal Repellents."

(Continued)

*Primary Examiner* — Yvonne Abbott-Lewis
(74) *Attorney, Agent, or Firm* — DT Ward, PC; Donna T. Ward; Christopher P. Sullivan

(57) ABSTRACT

The present invention provides compositions and methods for the control and management of wildlife populations (including domesticated animals) and pests such as rodents, birds including geese, deer and other herbivores such as rabbits, ground hogs, raccoons, moose and elk, tunneling animals such as moles, voles and gophers and insects, carnivores and other organisms such as predators. Specifically provided are FIFRA exemption-based formulations which may be applied to natural or artificial surfaces.

19 Claims, No Drawings

(56) References Cited

U.S. PATENT DOCUMENTS

| | | |
|---|---|---|
| 6,969,521 B1 | 11/2005 | Gonzalez et al. |
| 7,037,515 B2 | 5/2006 | Kalafsky et al. |
| 7,204,054 B2 | 4/2007 | Mayo et al. |
| 7,357,946 B2 * | 4/2008 | Adamoli, Jr. .......... A01N 25/08 111/916 |
| 7,605,096 B2 | 10/2009 | Tomarchio et al. |
| 7,712,249 B1 | 5/2010 | Modlin et al. |
| 7,846,463 B2 | 12/2010 | Johal |
| 7,858,127 B2 | 12/2010 | Overman |
| 7,947,298 B2 | 5/2011 | La Torre |
| 7,956,092 B2 | 6/2011 | Knoblauch et al. |
| 8,101,657 B2 | 1/2012 | Yamada et al. |
| 8,404,260 B2 | 3/2013 | Reid et al. |
| 8,753,676 B2 | 6/2014 | Kritzman et al. |
| 8,771,718 B2 | 7/2014 | Scialdone et al. |
| 2002/0102281 A1 | 8/2002 | Auberger et al. |
| 2002/0110576 A1 | 8/2002 | Messina |
| 2003/0175369 A1 | 9/2003 | Khazan-enache |
| 2004/0111962 A1 * | 6/2004 | Iizuka .................. A01C 21/00 47/57.6 |
| 2004/0127362 A1 | 7/2004 | Hiromoto |
| 2004/0128908 A1 * | 7/2004 | Neumann .............. A01N 37/12 47/57.6 |
| 2004/0131627 A1 | 7/2004 | Werdyger |
| 2005/0008714 A1 | 1/2005 | Enan |
| 2005/0214337 A1 | 9/2005 | McGee et al. |
| 2005/0233930 A1 | 10/2005 | Cheung et al. |
| 2006/0029630 A1 | 2/2006 | Overman |
| 2006/0083763 A1 | 4/2006 | Neale et al. |
| 2006/0236604 A1 * | 10/2006 | Hesse ...................... A01C 1/06 47/57.6 |
| 2006/0263326 A1 | 11/2006 | Weiser |
| 2007/0031463 A1 | 2/2007 | Fotinos et al. |
| 2007/0092544 A1 | 4/2007 | Mills |
| 2007/0224232 A1 | 9/2007 | Sherwood |
| 2007/0248688 A1 | 10/2007 | La Torre |
| 2007/0264297 A1 | 11/2007 | Scialdone et al. |
| 2008/0020078 A1 | 1/2008 | Enan |
| 2008/0069785 A1 | 3/2008 | Jones |
| 2008/0120900 A1 | 5/2008 | O'neal et al. |
| 2008/0166415 A1 | 7/2008 | Markus et al. |
| 2008/0181968 A1 | 7/2008 | Besendorfer |
| 2008/0274072 A1 | 11/2008 | Manolas et al. |
| 2009/0238787 A1 | 9/2009 | Finke et al. |
| 2009/0253612 A1 | 10/2009 | Mushock et al. |
| 2009/0258950 A1 | 10/2009 | Knoblauch |
| 2009/0263515 A1 | 10/2009 | Bessette |
| 2010/0003341 A1 | 1/2010 | Besendorfer |
| 2010/0040705 A1 | 2/2010 | Komai et al. |
| 2010/0074860 A1 | 3/2010 | Kupfer et al. |
| 2010/0104666 A1 | 4/2010 | Cox |
| 2010/0224697 A1 | 9/2010 | Modlin et al. |
| 2010/0247684 A1 | 9/2010 | Reid et al. |
| 2010/0260862 A1 | 10/2010 | Cox |
| 2010/0263274 A1 * | 10/2010 | Corak ................... A01H 4/006 47/57.6 |
| 2011/0135764 A1 | 6/2011 | Enan |
| 2012/0251641 A1 | 10/2012 | Enan et al. |
| 2013/0019813 A1 * | 1/2013 | Rubin .................. A01G 31/001 119/712 |
| 2013/0084535 A1 | 4/2013 | Braun et al. |
| 2013/0156839 A1 | 6/2013 | Messina et al. |
| 2013/0164361 A1 | 6/2013 | Enan |
| 2013/0183392 A1 | 7/2013 | Moore et al. |
| 2014/0178444 A1 | 6/2014 | Stadler et al. |
| 2014/0220164 A1 | 8/2014 | Manhas et al. |
| 2014/0242199 A1 | 8/2014 | Manhas et al. |
| 2014/0335140 A1 | 11/2014 | Hoag et al. |

FOREIGN PATENT DOCUMENTS

| | | |
|---|---|---|
| WO | 03013243 A1 | 2/2003 |
| WO | 2010019141 A1 | 2/2010 |
| WO | 2011/142918 | 11/2011 |
| WO | 2013155438 A1 | 10/2013 |

OTHER PUBLICATIONS

Harris, C.E., E.E. Simonne, P. Codreanu, and J. Eakes. 2000. Deer response to selected plant extracts. HortScience 35(3):466-467.

* cited by examiner

COMBINATION ANIMAL REPELLENTS

CROSS REFERENCE TO RELATED APPLICATIONS

This application is a continuation-in-part of U.S. National Stage patent application Ser. No. 14/356,988, filed May 8, 2014, entitled "Combination Animal Repellents," which is a 35 U.S.C. §371 U.S. National Stage Entry of International Application No. PCT/US2012/061817 filed Oct. 25, 2012, entitled "Combination Animal Repellents," which claims the benefit of priority of U.S. Provisional Patent Application No. 61/557,985 filed on Nov. 10, 2011, entitled "Combination Animal Repellents," and U.S. Provisional Patent Application No. 61/638,590 filed on Apr. 26, 2012, entitled "Combination Animal Repellents," the contents of each of which are hereby incorporated by reference in their entirety.

FIELD OF THE INVENTION

The invention relates to an animal and/or insect repellent and, in particular, to broad spectrum repellent compositions which will repel a variety of pests and which can be applied to a wide range of surfaces and substrates. Methods of use are also disclosed.

BACKGROUND OF THE INVENTION

The encroachment of human habitation on heretofore rural areas has exacerbated existing problems of pest control. In recent years suburban backyards and public green spaces have been invaded by exploding deer populations and fowl who take up residence on ponds and in public areas near water fouling the surface or surrounding land area. Insect pests and rodents are also becoming more prevalent in suburban, urban and rural areas. Further, with the changes in climate and the expanding human habitation into rural areas livestock and household pets have become increased targets for predators.

Synthetic and often toxic chemical control means have long been used to manage pest and animal movement and populations. However, with increasing public awareness of health issues regarding the impact on humans and the environment exposed to such chemical compounds, much effort has been expended in the identification of more benign and natural control measures.

To this end, legislative steps have been taken to categorize certain natural compounds as safe for use and hence exempt from certain government regulations. Such active ingredients qualifying for Federal Insecticide, Fungicide, and Rodenticide Act (FIFRA) exemption include castor oil (U.S.P. or equivalent), linseed oil, cedar oil, malic acid, cinnamon and cinnamon oil, mint and mint oil, citric acid, peppermint and peppermint oil, citronella and citronella oil, 2-Phenethyl propionate (2-phenylethyl propionate), cloves and clove oil, potassium sorbate, corn gluten meal, putrescent whole egg solids, corn oil, rosemary and rosemary oil, cottonseed oil, sesame (includes ground sesame plant) and sesame oil, dried blood, sodium chloride (common salt), eugenol, sodium lauryl sulfate, garlic and garlic oil, soybean oil, geraniol, thyme and thyme oil, geranium oil, white pepper, sodium lauryl sulfate, zinc metal strips (consisting solely of zinc metal and impurities) and lemongrass oil.

Despite the strong incentive to develop natural and safe pesticides and animal repellents, there remains a long-felt need for compositions that are as effective (or more effective) than the chemical toxins currently in use to mitigate the economic and health impact of pests on humans.

SUMMARY OF THE INVENTION

The present invention provides compositions for use as single- or multi-species (broad spectrum) repellent that alters the movement of animals and/or insects. As such, the present invention is directed to geraniol oil, rosemary oil, putrescent whole egg solids and/or other FIFRA active ingredient based combination compositions for use as single- or multi-species (broad spectrum) animal and/or insect repellents. In combination with the pest management systems described herein, the invention also embraces the use of attractants. Further aspects of the invention include the application of the formulations of the invention by contacting or impregnation to one or more substrates or surfaces. The formulations of the present invention provide further advantages in that most comprise only natural ingredients or ingredients not requiring EPA approval making them useful for application by homeowners and non-licensed applicators as well as for professional use.

In one embodiment, the present invention provides binary repellent compositions which comprise geraniol oil. In another embodiment, the invention provides ternary repellent compositions which comprise geraniol oil and either mint or castor oil alone or in combination with other ingredients. In one embodiment, the present invention provides a repellent composition comprising: (a) about 0.05 to about 30 weight percent of geraniol oil; (b) about 0.05 to about 15 weight percent of mint oil; (c) about 0.2 to about 35 weight percent of castor oil; (d) about 0.002 to about 9.3 weight percent of sodium lauryl sulfate; (e) about 0.01 to about 10 weight percent of kaolin; (f) about 0.1 to about 7.5 weight percent of xanthan gum; and (g) about 55 to about 95.6 weight percent of water. As such the repellent compositions may be formulated as an aqueous solution or mixture or as a concentrate.

In one embodiment, the present invention provides a repellent composition comprising (a) about 3 to about 25 weight percent of geraniol oil; (b) about 0.1 to about 8.5 weight percent of mint oil; (c) about 0.75 to about 20.5 weight percent of castor oil; (d) about 0.005 to about 6.5 weight percent of sodium lauryl sulfate; (e) about 0.03 to about 5 weight percent of kaolin; (f) about 0.5 to about 4.5 weight percent of xanthan gum; and (g) about 60 to about 93 weight percent of water.

In another embodiment the repellent composition comprises (a) about 5 to about 20 weight percent of geraniol oil; (b) about 0.3 to about 5.5 weight percent of mint oil; (c) about 2.1 to about 7.2 weight percent of castor oil; (d) about 0.01 to about 1 weight percent of sodium lauryl sulfate; (e) about 0.05 to about 2 weight percent of kaolin; (f) about 0.1 to about 2.3 weight percent of xanthan gum; and (g) about 65 to about 91 weight percent of water.

In one embodiment, the present invention provides repellent compositions comprising rosemary oil either alone or in combination with geraniol oil and other ingredients. In another embodiment, the repellent composition comprises (a) about 0.05 to about 30 weight percent geraniol oil; (b) about 0.07 to about 8.5 weight percent rosemary oil; (c) about 0.05 to about 15 weight percent of mint oil; (d) about 0.2 to about 35 weight percent of castor oil; (e) about 0.01 to about 10 weight percent kaolin; (f) about 0.1 to about 7.5 weight percent xanthan gum; and (g) about 55 to about 95.6 weight percent of water.

In another embodiment, the repellent composition comprises (a) about 0.05 to about 30 weight percent geraniol oil;

(b) about 0.07 to about 8.5 weight percent rosemary oil; (c) about 0.05 to about 15 weight percent of mint oil; (d) about 0.2 to about 35 weight percent of castor oil; (e) about 0.01 to about 10 weight percent kaolin; (f) about 0.1 to about 7.5 weight percent xanthan gum; (g) about 55 to about 95.6 weight percent of water; and (h) about 0.05 to about 10 weight percent cinnamon oil.

The repellent compositions may be diluted with water at a ratio of from 1 to 34 parts water, from 5 to 25 parts water or from 10 to 15 parts water. The water may be selected from the group consisting of ionized, distilled, filtered, spring, purified, mineral, sterile, well, artesian, fluorinated and a mixture thereof. They may also comprise one or more carriers, surface-active agents, thickeners, preservatives, aromatics, adjuvants, dilute acids, natural occurring insecticides, sodium chloride or potassium soaps. Carriers may be selected from the group consisting of bentonite, fullers earth, additional clays, talc, chalk, quartz, attapulgite, montmorillonite or diatomaceous earth, vermiculite, highly dispersed silicic acid, alumina and silicates, calcite, marble, pumice, sepiolite and dolomite, inorganic and organic meals, sawdust, coconut shells, corn cobs and tobacco stalks.

Surface-active agents useful in the present compositions may be selected from the group consisting of polyethylene oxide esters of fatty acids, polyethylene oxide ethers of fatty alcohols, alkyl sulfates, alkyl sulfonates, aryl sulfonates, albumin hydrolyzates, and especially alkyl arylpolyglycol ethers, magnesium stearate, sodium oleate, lignin, sulfite waste liquors and methyl cellulose.

Thickeners useful in the present invention may be selected from the group consisting of agar, corn starch, potato starch and guar gum.

Adjuvants useful in the present invention may be selected from the group consisting of wetting agents, spreading agents, surfactants, sticking agents, adhesives, foam retardants, buffers, acidifiers, colorants and stabilizers.

The repellent compositions of the present invention may be applied via painting, brushing, mopping, spreading, banding, broadcasting, side-dressing, coating, rolling, bathing, dipping, immersing, soaking, adhering, sticking, rubbing, wiping, impregnating, injecting, embedding, sealing, stippling, dotting, dabbing, stenciling, stamping, layering, spackling, sprinkling, aerosolizing, misting, dusting, fumigation, aerial application, vaporizing, pouring and combinations thereof. The term aerial application includes, but is not limited to, distribution from an aircraft.

The present invention further provides for an animal repellent substrate which may be coated with a geraniol oil repellent composition, or the substrate may be impregnated with a geraniol oil repellent composition. In one embodiment, the substrate coated may be a particulate selected from kaolin, crushed eggshell, nutshells, and corn having a particle size distribution of about dustless fine particles to about one-quarter inch overall thickness. In another embodiment, the coated surface is a ribbon or tape which may further comprise an adhesive. In a further embodiment, the ribbon or tape may be made from natural fibers or be substantially biodegradable.

The present invention further provides for methods of repelling an animal or insect from a surface, substrate or area comprising preparing the repellent composition containing geraniol oil and applying the repellent to a surface, substrate or area. The surface may be selected from the surface of plants, trees, grass, water, walks, parking lots, buildings, skin, fur or pelt of an animal or human, or an article of clothing.

The present invention further provides for methods of deterring predators from an area and/or animal comprising preparing a repellent composition containing geraniol and applying the repellent to a surface, substrate or area. The surface, substrate or area may be selected from, but is not limited to, the skin, fur or pet of an animal, an article of clothing, leashes, tags, collars, harnesses, ear tags, saddles, reins, blankets, farm structures, barns, pastures, grazing areas, stables, animal feed, feeding apparatus, fencing and/or other animal containment apparatus, shrubs, trees, ground cover, rocks, grass, crops, brush, dirt, soil, and other man-made apparatus and/or devices near livestock. The predator deterred may include, but is not limited to, lions, tigers, bears, bobcats, lynx, coyotes, wolves, wild and domestic dogs, foxes, hogs, mountain lions, weasels, mink, snakes, raccoons, skunks, opossums, domestic cats and badgers.

In some embodiments, the present invention provides a method of preparing a repellent seed composition comprising preparing a repellent formulation comprising 5.0 to 7.5 weight percent of geraniol oil; 2.0 to 5.0 weight percent of castor oil; 6.0 to 9.0 weight percent of peppermint oil; 2.0 to 8.0 weight percent of rosemary oil; 4.0 to 8.0 weight percent of cinnamon oil; 0.1 to 0.5 weight percent of xanthan gum; 0.9 to 2.0 weight percent of kaolin clay; and 60 to 80 weight percent of water; and treating seeds by combining the repellent formulation with the seeds at a ratio of about 10 g of repellent formulation per 1 pound of seeds. In some cases, the treated seeds are further allowed to dry. In a further embodiment, the repellent formulation comprises 5.5 weight percent of geraniol oil; 2.5 weight percent of castor oil; 6.6 weight percent of peppermint oil; 4.5 weight percent of rosemary oil; 4.9 weight percent of cinnamon oil; 0.15 weight percent of xanthan gum; 1.1 weight percent of kaolin clay; and 74.75 weight percent of water.

In other embodiments, the present invention provides a repellent seed composition comprising 5.5 weight percent of geraniol oil; 2.5 weight percent of castor oil; 6.6 weight percent of peppermint oil; 4.5 weight percent of rosemary oil; 4.9 weight percent of cinnamon oil; 0.15 weight percent of xanthan gum; 1.1 weight percent of kaolin clay; and 74.75 weight percent of water. In some cases, the invention further provides a method of reducing or eliminating seed consumption by pests comprising the use of such a repellent seed composition. According to such methods, seed consumption by pests may be reduced or eliminated for a period of from about 5 weeks to about 50 weeks and/or a period of from about 2 weeks to about 10 weeks. In some cases, repellent seed compositions comprise grass seeds.

According to some embodiments, the present invention provides a method of storing seeds comprising preparing a repellent seed composition by combining seeds with a repellent formulation at a ratio of 10 g of repellent formulation per pound of seed, wherein the repellent formulation comprises 5.5 weight percent of geraniol oil; 2.5 weight percent of castor oil; 6.6 weight percent of peppermint oil; 4.5 weight percent of rosemary oil; 4.9 weight percent of cinnamon oil; 0.15 weight percent of xanthan gum; 1.1 weight percent of kaolin clay; and 74.75 weight percent of water; allowing the repellent seed composition to dry; and storing the repellent seed composition.

In some embodiments, the present invention provides a method of preparing a granular repellent composition comprising preparing a concentrated repellent formulation comprising 0.05 to 30 weight percent of geraniol oil; 0.2 to 55 weight percent of castor oil; 10 to 25 weight percent of peppermint oil; 15 to 25 weight percent of rosemary oil; 5 to 20 weight percent of cinnamon oil; 0.01 to 5 weight percent of xanthan gum; 0.01 to 5 weight percent of kaolin clay; and 0 to 69.73 weight percent of water; and treating a granular material by combining the concentrated repellent formulation with granular material at a ratio of about 10 g of concentrated repellent formulation per 1 pound of granular material to about 30 g of the concentrated repellent formulation per 1 pound of granular material. In some cases, the granular material is allowed to dry.

In some embodiments, the present invention provides a method of preparing a granular repellent composition comprising preparing a concentrated repellent formulation comprising 5.75 weight percent of geraniol oil; 20 weight percent of castor oil; 16.49 weight percent of peppermint oil; 21.57 weight percent of rosemary oil; 10.8 weight percent of cinnamon oil; 0.23 weight percent of xanthan gum; 1.1 weight percent of kaolin clay; and 24.06 weight percent of water; and combining the concentrated repellent formulation with a granular material at a ratio of about 10 g of concentrated repellent formulation per 1 pound of granular material to about 30 g of the concentrated repellent formulation per 1 pound of granular material. In some cases, the granular material comprises crushed walnut shells.

In some embodiments, the present invention provides a granular repellent composition wherein a concentrated repellent formulation comprising 5.75 weight percent of geraniol oil; 20 weight percent of castor oil; 16.49 weight percent of peppermint oil; 21.57 weight percent of rosemary oil; 10.8 weight percent of cinnamon oil; 0.23 weight percent of xanthan gum; 1.1 weight percent of kaolin clay; and 24.06 weight percent of water is combined with crushed walnut shells at a ratio of about 10 g of concentrated repellent formulation per 1 pound of crushed walnut shells to about 30 g of the concentrated repellent formulation per 1 pound of crushed walnut shells.

According to some embodiments, the present invention provides a method of repelling pests from an area comprising the use of a granular repellent composition. In some cases, the pest is a rodent selected from the group consisting of mice, rabbits, squirrels, and groundhogs. In some cases, the pest is a groundhog and the area comprises a groundhog borough. According to such embodiments, the granular repellent composition may be applied inside and around the groundhog borough. In some cases, the granular repellent composition may be applied at least twice.

DETAILED DESCRIPTION OF THE INVENTION

The present invention provides compositions for use as single- or multi-species (broad spectrum) repellent that alters the movement of animals and/or insects. As such, the present invention is directed to geraniol oil, rosemary oil, putrescent whole egg solids and/or other FIFRA active ingredient based combination compositions for use as single- or multi-species (broad spectrum) animal and/or insect repellents. In combination with the pest management systems described herein, the invention also embraces the use of attractants. Further aspects of the invention include the application of the formulations of the invention by contacting or impregnation to one or more substrates or surfaces. The formulations of the present invention provide further advantages in that most comprise only natural ingredients or ingredients not requiring EPA approval making them useful for application by homeowners and non-licensed applicators as well as for professional use.

DEFINITIONS

A "repellent" as used herein is any composition or formulation that makes unattractive to pests a habitat, food source or other site ordinarily sought or frequented. The term "pest" is intended to include living organisms that occur where they are not wanted or that cause damage to crops or food or turf or humans or other animals. Examples of pests include, but are not limited to, insects, mice, squirrels, reptiles, rodents and other animals (e.g., predators, household pets and wild life), unwanted plants (weeds), fungi, microorganisms such as bacteria and viruses, and prions.

An "attractant" as used herein is any composition or formulation that makes attractive to pests a habitat, food source or other site which may be frequented or traversed by the pests.

"Alter the movement" as used herein refers to the ability of a formulation to change the mobility or direction of a pest (an animal and/or insect). For example, a repellent formulation applied to a surface may "alter the movement" of such insects by making a region of application near the surface unattractive to the insects and prevent the insects from approaching the surface.

"Predators" as used herein refers to an organism that preys on other organisms. Predators are usually animals that live by preying on other organisms for food. A non-limiting list of predators include lions, tigers, bears, bobcats, lynx, coyotes, wolves, wild and domestic dogs, foxes, hogs, mountain lions, weasels, mink, snakes, raccoons, skunks, opossums, domestic cats, and badgers. "Prey" as used herein refers to an organism that is hunted and killed by another organism for food. For example, many predators may hunt and eventually kill their prey such as, but not limited to, lions preying upon a buffalo, coyotes preying on livestock, and foxes preying on chickens.

Specifically, it has been discovered that the combination of one or more essential oils with one or more herb oils provide superior animal and/or insect repellent properties. As such, the components of the repellent compositions of the present invention function in a synergistic manner to provide multiple layers of repulsion. The repulsive effect is broad spectrum with regard to the number of animal and/or insect species repelled thus avoiding the necessity of applying multiple compositions to repel various animal pests, hence the compositions and their formulations broad spectrum repellents. "Broad spectrum," as used in the context of a repellent, means that the repellent possesses activity against multiple species of animals, insects and/or organisms.

As used herein, an "essential oil" is any hydrophobic liquid containing volatile aromatic compounds from plants. They are also known as volatile or ethereal oils, or simply as the "oil of" the plant material from which they were extracted, such as oil of clove. The term "essential" indicates that the oil carries distinctive scent (essence) of the plant. Essential oils are typically extracted by distillation and hence may be concentrated. Other processes include expression and solvent extraction. Essential oils may include sub-categories of oils such as "herb oils" and "mint oils". Among essential oils are *eucalyptus* oil and castor oil. The essential oils also include mint oil, jasmine oil, camphor oil, hinoki oil, tohi oil, pomegranate oil, turpentine oil, cinnamon oil, bergamot oil, mandarin oil, calamus oil, pine oil, lavender oil, bay oil, clove oil, hiba oil, rose oil, lemon oil, thyme oil, peppermint oil, rose oil, sage oil, menthol, cineole, eugenol, citral, citronellal, borneol, linalool, geraniol, camphor, thymol, spilanthole, pinene, limonene, and terpene compounds.

The term "herb oil" as used herein refers to any of the oils derived from herbs. An "herb" is a plant lacking a permanent woody stem. Among the preferred herb oils are mint and geranium oils with geraniol oil being most preferred.

Repellent compositions of the present invention may comprise at least one FIFRA active ingredient such as, but not limited to, geraniol oil, rosemary oil, mint, mint oil, cinnamon oil, clove oil, eugenol, putrescent whole egg solids, castor oil, sodium lauryl sulfate, sodium chloride, potassium sorbate and one inert ingredient such as, but not limited to, xanthan gum, sodium sulfate, kaolin (clay) and water.

The term "FIFRA active ingredient" refers to the active ingredients exempted under 25(b) of the Federal Insecticide, Fungicide, and Rodenticide Act (FIFRA). Examples of FIFRA active ingredients include castor oil (U.S.P. or equivalent), linseed oil, cedar oil, malic acid, cinnamon and cinnamon oil, mint and mint oil, citric acid, peppermint and peppermint oil, citronella and citronella oil, 2-Phenethyl propionate (2-phenylethyl propionate), cloves and clove oil, potassium sorbate, corn gluten meal, putrescent whole egg solids, corn oil, rosemary and rosemary oil, cottonseed oil, sesame (includes ground sesame plant) and sesame oil, dried blood, sodium chloride (common salt), eugenol, sodium lauryl sulfate, garlic and garlic oil, soybean oil, geraniol, thyme and thyme oil, geranium oil, white pepper, sodium lauryl sulfate, zinc metal strips (consisting solely of zinc metal and impurities) and lemongrass oil.

The term "inert ingredient" refers to the listing of inert ingredients approved for nonfood use. Examples of inert ingredients include, but are not limited to, xanthan gum, sodium sulfate, kaolin (clay) and water.

The repellent compositions may optionally comprise further components including, but not limited to, carriers, thickeners, surface-active agents, preservatives, aromatics, deodorizers, antibacterial agents, antifungal agents, antimicrobial agents, biocide agents, sunscreen active and one or more of several types of adjuvant including, but not limited to, wetting agents, spreading agents, sticking agents, foam retardants, buffers and acidifiers. The term "antibacterial agents" refers to substances which may destroy or inhibit the growth of bacteria; "antifungal agents" refers to substances which may destroy or inhibit the growth of fungi; "antimicrobial agents" refers to substance which may kill or inhibit the growth of microorganisms and "biocide agents" refers to chemical substances or microorganisms which may be capable of destroying living organisms. As used herein, "sunscreen active" is an additive that may absorb or reflect some of the ultraviolet radiation from a surface exposed to sunlight. The repellent compositions of the present invention may also be formulated in a combination with commercially available pesticides or insecticides (natural or synthetic).

The repellent properties of the compositions of the present invention qualify them as pesticides. According to the Environmental Protection Agency (EPA) and as used herein a "pesticide" is any substance or mixture of substances intended for: preventing, destroying, repelling, or mitigating any pest. They also include any substance or mixture of substances intended for use as a plant regulator, defoliant, or desiccant.

Typically, the repellent compositions are prepared as a concentrate and diluted to application strength or admixed with the appropriate particulate matter when used.

Concentrates may be diluted with water or suitable solvent at the time of use or it may be in ready-to-use form whereby the formulation requires no further manipulation before use. The term "concentrate" is used herein to describe a repellent composition or formulation which is in condensed form. A concentrate of the present invention is not necessarily without the presence of any diluent, e.g. water. Hence, a concentrate may be in liquid, solid, or gel form. It may be impregnated in or mixed with another substance which allows for distribution into the environment such as in a humidifier, diffuser, candle or air freshener.

For all components of the repellent compositions or their formulations, values in increments of the smallest measured value (e.g., for geraniol oil, 0.05%) are embraced within the ranges specified. For example, the range from 0.05% to 30% embraces the weight percentages of 0.05%, 0.10%, 0.15% . . . 29.9%, 29.95% and 30%.

Further, as used throughout the specification the term "about" is defined as plus or minus 10% of the stated value.

As used herein, the term "bait" as it relates to pest is any substance or composition in any form which lures or entices, whether chemically or physically (such as a visual cue), a pest. Baits include, but are not limited to, those made by Raid, Term, Combat, Jensen, Hot Shot, Woodstream, SC Johnson, Advance, MaxForce, or any commercially available bait or combination thereof and the like. A "bait" may also be an attractant.

As used herein, a "trap" or "bait box" means any container or structure which may contain a bait, attractant or repellent and which is capable of containing one or more pests.

Units of measure used herein embrace both standard units and metric units. It is to be understood that where repellent or attractant compositions are measured, formulated or packaged as liquids, the units may be in increments of ounces, cups, pints, quarts, gallons, barrels, or portions thereof. They may also be in increments of milliliters, cubic centimeters, deciliters, liters, cubic meter or portions thereof.

It is to be understood that where repellent or attractant compositions are measured, formulated or packaged as solids, the units may be in increments of ounces, pounds, tons, or portions thereof. They may also be in increments of milligrams, grams, kilograms, metric tons or portions thereof.

Coverage, as it relates to the effectiveness of the repellent or attractant radius of the devices of the invention, may be expressed in inches, feet, square feet, yards, square yards, acres, square acres, or portions thereof. They may also be in increments of millimeters, square millimeters, centimeters, square centimeters, meters, square meters, hectares, kilometers, square kilometers or portions thereof. Conversion between the standard and metric systems is readily understood in the art and particularly by those of skill in the art. Therefore, the present invention which teaches formulations in weight percent and ratios for dilution of concentrate are not limited to any particular system of measurement. For example, while the instant examples may describe the use of a single system, the present invention is just as clear on the formulation of a quart of repellent composition as a liter of repellent composition.

Geraniol Oil

In one embodiment, the repellent compositions and formulations thereof may contain geraniol oil. While some of the compositions of the present invention are referred to as "geraniol-based" this designation is not intended to imply any specific quantity or proportion of geraniol. It is merely to convey that the compositions contain geraniol.

Geraniol, (3,7-dimethyl-2,6-octadien-1-ol; CAS Reg. No. 106-24-1; $C_{10}H_{18}O$) is a clear to pale yellow monoterpenoid alcohol which exists as an oily liquid. It is insoluble in water, but soluble in most common organic solvents. It has a rose-like odor, for which it is commonly used in perfumes. It is the primary part of oil-of-rose and palmarosa oil. It also occurs in small quantities in Geranium, Lemon, Citronella, and many other essential oils. Geraniol may be derived directly from geranium plants engineered to produce larger amounts of geraniol or from lemon grass or other herbs. It is typically extracted from geranium oil through a refining process.

While geraniol is used in insect repellants or deterrents to repel mosquitoes, house flies, stable flies, horn flies, cockroaches, fire ants, fleas, gnats, dog ticks, lone star ticks, no-see-ums, mite, crickets, earwigs, silverfish and lice, it is not known to have bird or non-insect repellant functionalities.

Surprisingly, it has been discovered that geraniol oil, in combination with castor oil, and mint does indeed have both bird and non-insect repellent properties as well as the killing of some organisms including scales. Such combinations are detailed in published co-pending application International Application PCT/US2011/031901 filed Apr. 11, 2011, the contents of which are incorporated herein by reference in their entirety.

According to the present invention, geraniol oil may be present in the compositions of the present invention from about 0.05% by weight to about 30% by weight, but may be higher in concentrated formulations. In one embodiment, geraniol is present in an amount from 3-25% by weight. In a further embodiment it is present in an amount by weight of from 5-20%. In addition, geraniol oil may be present in amounts between or bounded by those recited herein. For example, the weight percentages 0.05-1%, 2-3%, 20-30%, 3-10%, 15-25%, 5-10%, and 15-20% are within the scope of the invention.

Rosemary Oil

In one embodiment, the repellent compositions and formulations of the present invention may contain rosemary oil. While some of the compositions of the present invention are referred to as "rosemary oil-based" this designation is not intended to imply any specific quantity or proportion of rosemary oil but it is merely to convey that all of the compositions contain rosemary oil.

Surprisingly, it has been discovered that rosemary oil (CAS Reg. No. 8000-25-7), in combination with castor oil, and mint does have bird, insect and animal repellent properties. Such combinations are detailed in published co-pending application International Application PCT/US2008/072993 filed Aug. 13, 2008 and U.S. patent application Ser. No. 13/058,424 filed Apr. 7, 2011 the contents of which are incorporated herein by reference in their entirety.

According to the present invention, rosemary oil, when present, may be present in the compositions of the present invention from about 0.05% by weight to about 30% by weight, but may be higher in concentrated formulations. In one embodiment, rosemary oil is present in an amount from 3-25% by weight. In a further embodiment it is present in an amount by weight of from 5-20%. In addition, rosemary oil may be present in amounts between or bounded by those recited herein. For example, the weight percentages 0.05-1%, 2-3%, 20-30%, 3-10%, 15-25%, 5-10%, and 15-20% are within the scope of the invention.

Putrescent Whole Egg Solid

In one embodiment, the repellent compositions and formulations thereof may contain putrescent whole egg solid. While some of the compositions of the present invention are referred to as "putrescent whole egg solid-based" this designation is not intended to imply any specific quantity or proportion of putrescent whole egg solid. It is merely to convey that the compositions may contain putrescent whole egg solid.

Putrescent whole egg solids (CAS Reg. No. 51609-52-0) such as, but not limited to, inedible egg powder, dried whole egg, or powdered inedible egg solids), may be produced from eggs which the USDA has declared inedible for human consumption due to cracked shells, excessive blood spots or other imperfections not conforming to standards set for food use. They may be produced by centrifuging whole eggs, which have been cracked or broken, to separate the shell from the liquid egg. The liquid egg may then be pumped through a strainer to remove foreign material (e.g., shell pieces) then placed in a holding tank or passed through a pasteurizer, cooled, spray dried and packaged for storage. The powdered eggs may be hydrated at the time of use which initiates the decaying process.

According to the present invention, putrescent whole egg solid may be present in the repellent compositions from about 0.01% by weight to about 15% by weight. In one embodiment, putrescent whole egg solids are present in an amount from 0.1-13% by weight. In a further embodiment, it is present in an amount by weight from 0.15-10%. In addition, putrescent whole egg solids may be present in amounts between or bounded by those recited herein. For example, the weight percentages 0.05-1%, 2-3%, 1-10%, 3-10%, 10-15%, and 5-10% are within the scope of the invention.

Cinnamon Oil

In one embodiment, the repellent compositions and formulations of the present invention may contain cinnamon oil. Cinnamon oil (CAS Reg. No. 8015-91-6) has been found to have properties that repel household pets such as, but not limited to, cats and dogs. Cinnamon oil in combination with clove oil and eugenol has also been found to have snake repellent properties.

According to the present invention, cinnamon oil may be present in the repellent compositions from about 0.05% by weight to about 10% by weight, but may be higher in concentrated formulations. In one embodiment, cinnamon oil is present in an amount from 0.1-8% by weight. In a further embodiment, it is present in an amount from 0.15-5%. In addition, cinnamon oil may be present in amount between or bounded by those recited herein. For example, the weight percentages 0.01-1%, 0.1-2%, 0.2-5%, 1-5% and 0.2-10% are within the scope of the invention.

Clove Oil

In one embodiment, the repellent compositions and formulations of the present invention may contain clove oil. Clove oil (CAS Reg. No. 800-34-8) in combination with cinnamon oil and eugenol has been found to have snake repellent properties.

According to the present invention, clove oil may be present in the repellent compositions from about 0.05% by weight to about 10% by weight. In one embodiment, clove oil is present in an amount from 0.1-8% by weight. In a further embodiment, it is present in an amount from 0.15-5%. In addition, clove oil may be present in amount between or bounded by those recited herein. For example, the weight percentages 0.01-1%, 0.1-2%, 0.2-5%, 1-5% and 0.2-10% are within the scope of the invention.

Eugenol

In one embodiment, the repellent compositions and formulations of the present invention may contain eugenol. Eugenol (CAS Reg. No. 97-53-0) is a phenolic compound found at high levels in clove oil. Eugenol is known as an insecticide for its ability to kill some insects. Eugenol, when used in combination with clove oil and cinnamon oil, has also been found to have snake repellent properties.

According to the present invention, eugenol may be present in the repellent compositions from about 0.05% by weight to about 10% by weight. In one embodiment, eugenol is present in an amount from 0.1-8% by weight. In a further embodiment, it is present in an amount from 0.15-5%. In addition, eugenol may be present in amount between or bounded by those recited herein. For example, the weight percentages 0.01-1%, 0.1-2%, 0.2-5%, 1-5% and 0.2-10% are within the scope of the invention.

Castor Oil

The repellent compositions of the present invention may include the essential oil, castor oil. Castor oil is a vegetable oil derived from the seed of the castor plant, *Ricinus communis*. Castor oil (CAS number 8001-79-4) is a colorless to very pale yellow liquid with mild or no odor or taste. It is a triglyceride in which approximately ninety percent of fatty acid chains are ricinoleic acid but which may comprise oleic and linoleic acids.

According to the present invention castor oil may be present in the compositions of the present invention from about 0.02% by weight to about 55% by weight. In one embodiment, castor oil is present in an amount from 0.75%-20.5% by weight. In a further embodiment it is present in an amount by weight of from 2.1-7.2%. In addition, castor oil may be present in amounts between or bounded by those recited herein. For example, the weight percentages 0.02 to 5%, 20-35%, 20-55%, 0.75-10%, 15-20.5%, 2.1-5%, and 3-7.2% are within the scope of the invention.

In one embodiment, triglycerides that comprise any combination of ricinoleic, oleic and/or linoleic acids may be substituted for, or mixed with, castor oil in the compositions of the invention.

In certain formulations of repellent, castor oil is an optional ingredient. For example, in applications designed to repel deer, rabbits, groundhogs and other herbivores, castor oil is optional.

Mint Oil

Repellent formulations of the present invention may include one or more mint oils. Mint oil is derived from one or more of the approximately 25 species of plants in the genus *Mentha* or the many hundreds of varieties of flowering plants in the family Lamiaceae (Mint Family). Species within *Mentha* have a distribution across Europe, Africa, Asia, Australia, and North America. Several mint hybrids commonly occur. The most common and popular mints for cultivation are peppermint (*Mentha piperita*) and spearmint (*Mentha spicata*).

Mint oil is known as an insecticide for its ability to kill some common pests like wasps, hornets, ants and cockroaches. The duration and scope of effectiveness of mint oil may be increased by adding *eucalyptus* oil, citronella, soybean oil, neem oil, and/or Deet.

According to the present invention mint oil may be present in the repellent compositions of the present invention from about 0.05% by weight to about 15% by weight, but may be higher in concentrated formulations. In one embodiment, mint oil is present in an amount from 0.1%-8.5% by weight. In a further embodiment it is present in an amount by weight of from 0.3-5.5%. In addition, mint oil may be present in amounts between or bounded by those recited herein. For example, the weight percentages 0.05-7%, 8-15%, 0.1-4%, 4-8.5%, 0.3-3%, and 3-5.5% are within the scope of the invention. Any of the known mint oils may be used in the compositions of the present invention. These include, but are not limited to, water mint, or marsh mint, corn mint, wild mint, japanese peppermint, field mint, pudina, asian mint, Australian mint, pennyroyal, bergamot mint, wrinkled-leaf mint, Dahurian Thyme, slender mint, forest mint, horse mint, Corsican mint, garden mint, spearmint, curly mint, apple mint, pineapple mint and gray mint.

In certain formulations of repellent, mint oil is an optional ingredient. For example, in applications designed to repel moles, mint oil is optional.

Sodium Lauryl Sulfate

Sodium lauryl sulfate (SLS), ($C_{12}H_{25}SO_4$.Na) is an anionic surfactant used in many cleaning and hygiene products. The molecule has a tail of 12 carbon atoms, attached to a sulfate group, giving the molecule the amphiphilic properties favorable in a detergent. SLS is a highly effective surfactant. As used herein, the term "surfactant" means any substance which reduces the surface tension of a liquid. Surfactants may act as detergents, wetting agents, emulsifiers, foaming agents, and dispersants. According to the present invention, SLS may be added to the repellent compositions as an adjuvant thereby improving the properties of the compositions or the ease of use of said compositions.

According to the present invention SLS may be present in the compositions of the present invention from about 0.002% by weight to about 9.3% by weight. In one embodiment, SLS is present in an amount from 0.005%-6.5% by weight. In a further embodiment it is present in an amount by weight of from 0.01-1%. In addition, SLS may be present in amounts between or bounded by those recited herein. For example, the weight percentages 0.002-5%, 5-9.3%, 0.005-3%, 3-6.5%, 0.01-0.5%, 0.1-5% and 0.5-1% are within the scope of the invention. In formulations which are granular or substantially dry in nature, SLS may not be necessary.

Kaolin (Clay)

In its natural state kaolin is a white, soft powder consisting principally of the mineral kaolinite. It is commonly used in the manufacture of china (porcelain), paper, rubber and paints. When mixed with water in the range of 20 to 35 percent, it becomes plastic (i.e., it can be molded under pressure), and the shape is retained after the pressure is removed. With larger percentages of water, the kaolin forms a slurry, or watery (aqueous) suspension as kaolin is insoluble in water.

Modified kaolin is used in industry as a physical barrier-type crop protectant. In these formulations, it is sprayed on as a slurry, whereby the water evaporates, leaving a powdery film on the surfaces of leaves, stems, and fruit. The film acts to protect plants and deter insects. However, to be effective, the film must coat all parts of the fruit or plant.

In one embodiment of the present invention, kaolin may be added to the repellent compositions to improve adherence properties. It is not necessary that the repellent compositions containing kaolin described herein entirely coat or cover all parts of the surfaces or substrates treated in order to be effective repellents.

According to the present invention kaolin, when used, may be present in the compositions of the present invention from about 0.01% by weight to about 10% by weight. In one embodiment, kaolin may be present in an amount from about 0.01%-5% by weight. In another embodiment, kaolin may be present in an amount from about 0.03%-5% by weight. In a further embodiment it may be present in an amount by weight of from about 0.05-2%. In addition, kaolin may be present in amounts between or bounded by those recited herein. For example, the weight percentages 0.01-5%, 5-10%, 0.03-2%, 2-5%, 0.05-1%, and 1-2% are within the scope of the invention.

Xanthan Gum

Xanthan gum is a polysaccharide traditionally used as a food additive. In the present invention, xanthan gum may be used as a thickening agent. Xanthan gum is advantageous in liquid formulations but is not necessary in powder or other dry forms.

According to the present invention xanthan gum may be present in the compositions of the present invention from about 0.01% by weight to about 7.5% by weight. In one embodiment, xanthan gum may be present in an amount from about 0.01%-5% by weight. In another embodiment, xanthan gum is present in an amount from 0.5%-4.5% by weight. In a further embodiment it is present in an amount by weight of from 0.1-2.3%. In addition, xanthan gum may be present in amounts between or bounded by those recited herein. For example, the weight percentages 0.01-3%, 0.1-3%, 3-7.5%, 0.5-2%, 2-4.5%, 0.01-1%, and 1-2.3% are within the scope of the invention.

Potassium Sorbate

Potassium sorbate (CAS Reg. No. 7647-14-5) is the potassium salt of sorbic acid and is primarily used as a food preservative. According to the present invention potassium sorbate may be present in the repellent compositions of the present invention from about 0.001% by weight to about 5% by weight. In addition, potassium sorbate may be present in amounts between or bounded by those recited herein. For example, the weight percentages 0.001-5%, 0.01-5%, 0.01-0.04%, 0.3-3%, and 3-5.5% are within the scope of the invention.

Sodium Chloride

Sodium chloride (CAS Reg. No. 24634-61-5) is primarily used as a condiment and a food preservative. According to the present invention sodium chloride may be present in the repellent compositions of the present invention from about 0.001% by weight to about 5% by weight. In addition, sodium chloride may be present in amounts between or bounded by those recited herein. For example, the weight percentages 0.001-5%, 0.01-5%, 0.01-0.04%, 0.3-3%, and 3-5.5% are within the scope of the invention.

Repellent Formulations

The repellent compositions of the present invention may be formulated. A "formulation" as used herein is a combination of components prepared as per a formula. Formulations may be made for one or more particular applications or uses. The formulations of the present invention are also compositions while compositions may be formulated.

Formulations comprising the repellent compositions of the present invention may be prepared in any known manner, and may be in the form of liquid solutions (e.g., aqueous) or mixtures which are substantially dry. For instance, the repellent compositions may be mixed with conventional dispersible liquid diluents or carriers and/or dispersible solid carriers. They may be in the form of aqueous solutions, slurries or mixtures. The repellent composition can be mixed with carriers and the combination or just the repellent composition can be freeze-dried. As used herein, "freeze-dried" means a dehydration process used to preserve a material.

The pest management systems of the present invention may be used in combination with the repellent formulations of the invention or with attractants known in the art. Attractant formulations of the present invention may comprise of one or a combination of the following: sugar, honey, molasses, pheromones, plant oils, plant extracts, floral odors, proteins, salt, animal oils such as fish oil and the like, seeds, animal feed, livestock feed, nut shells such as walnut and/or peanut shells and the like, clay, sedimentary clay or clay-like earthy material (e.g., Fuller's earth) and the like, acetic acid mixtures such as, but not limited to, vinegar and the like, and sticky agents, adhesives including substances such as tanglewood and the like. The attractant composition may be applied in the form of aerosol, balm, cream, gel, lotion, mousse, patch, pump spray, roll on, solution, gel stick, solid stick, towelette, salve, ointment, powder, liquid, granules, candle, vapor, beads and the like. As used herein, "towelette" means a moistened piece of paper or cloth or the like. It is known to those in the art that "towelette" can also be known as a "wet wipe." A "patch", as used herein, means at least one piece of material which may be affixed to a surface such as skin, fabric, shoes or the like.

Attractants include compositions and formulations such as those known to those skilled in the art and also disclosed in U.S. Patent Application Nos. 20100074860 and 20090258950, the contents of which are incorporated herein by references in their entirety.

Repellent formulations of the present invention may comprise as a binary base formulation which includes at least a FIFRA active ingredient and one other ingredient selected from a FIFRA active ingredient and an inert ingredient.

In one embodiment, the base formulation comprises geraniol oil from 0.05 to 30 percent by weight in combination with one or more mint oils from 0.05 to 15 percent by weight. According to the invention, binary base formulations may also comprise geraniol oil from 0.05 to 30 percent by weight in combination with castor oil from 0.2 to 55 percent by weight. In another embodiment, the binary base formulation may comprise geraniol oil from 2 to 30 percent by weight in combination with a surfactant from 0.01 to 5 weight percent. A further embodiment may comprise geraniol oil from 2 to 30 percent by weight in combination with mint oil from 0.5 to 6 percent by weight, sodium lauryl sulfate from 0.01 to 6 percent by weight wherein other ingredients added in the formulation may be selected from, but not limited to, a thickener, a binder, a gelling agent, a solvent and a vegetable oil. The binary repellent compositions may be applied in the form of aerosol, balm, cream, gel, lotion, mousse, patch, pump spray, roll on, solution, gel stick, solid stick, towelette, salve, ointment, powder, liquid, granules, candle, vapor, beads and the like. Certain non-limiting examples of binary base formulations are shown in Table 1.

TABLE 1

Binary Base Repellent Formulations

| Component (CAS Reg. No) | Weight percent of Component Base Formulation 1 | Weight percent of Component Base Formulation 2 |
|---|---|---|
| Geraniol oil (106-24-1) | 0.05-30 | 0.05-30 |
| Mint oil | 0.05-15 | — |
| Castor oil (8001-79-4) | — | 0.2-55 |
| Other ingredients | 55-99.9 | 35-99.75 |

Further, ternary base formulations may be formed which include a FIFRA active ingredient. In one embodiment, a ternary base formulation comprises geraniol oil, mint oil and castor oil. The tertiary repellent compositions may be applied in the form of aerosol, balm, cream, gel, lotion, mousse, patch, pump spray, roll on, solution, gel stick, solid stick, towelette, salve, ointment, powder, liquid, granules, candle, vapor, beads and the like.

TABLE 2

Repellent Formulations

| Component (CAS Reg. No) | Weight percent of Component Base Formulation 3 |
|---|---|
| Geraniol oil (106-24-1) | 0.05-30 |
| Mint oil | 0.05-15 |
| Castor oil (8001-79-4) | 0.2-55 |
| Other ingredients | 5-99.7 |

Repellent formulations of the present invention may comprise as a ternary base formulation which includes rosemary oil and mint oil and cedar oil. In one embodiment, the base formulation comprises rosemary oil from 0.07 to 8.5 percent by weight in combination with one or more mint oils from 0.07 to 8.5 percent by weight and cedar oil from 2.5 to 40 percent by weight. A further embodiment may comprise rosemary oil from 0.1 to 4 percent by weight with mint oil from 0.1 to 4 percent by weight, cedar oil from 15 to 30 percent by weight wherein other ingredients added in the formulation may be selected from, but not limited to, a thickener, a binder, a gelling agent, a solvent and a vegetable oil. The ternary repellent compositions may be applied in the form of aerosol, balm, cream, gel, lotion, mousse, patch, pump spray, roll on, solution, gel stick, solid stick, towelette, salve, ointment, powder, liquid, granules, candle, vapor, beads and the like. Certain non-limiting examples of ternary base formulations are shown in Table 3.

TABLE 3

Repellent Formulations

| Component (CAS Reg. No) | Weight percent of Component Base Formulation 4 |
|---|---|
| Rosemary oil (8000-25-7) | 0.07-8.5 |
| Mint oil | 0.07-8.5 |
| Cedar oil (8001-79-4) | 2.5-40 |
| Other ingredients | 43-97.4 |

Repellent formulations of the present invention may comprise as a ternary base formulation which includes putrescent whole egg solids, cinnamon oil and clove oil. In one embodiment, the base formulation comprises putrescent whole egg solids from 0.01 to 15 percent by weight in combination with cinnamon oil from 0.05 to 10 percent by weight and clove oil from 0.05 to 10 percent by weight. A further embodiment may comprise putrescent whole eggs solids from 0.1 to 3 percent by weight with cinnamon oil from 0.1 to 3 percent by weight, clove oil from 0.1 to 3 percent by weight wherein other ingredients added in the formulation may be selected from, but not limited to, a thickener, a binder, a gelling agent, an acid, a solvent and a vegetable oil. The ternary repellent compositions may be applied in the form of aerosol, balm, cream, gel, lotion, mousse, patch, pump spray, roll on, solution, gel stick, solid stick, towelette, salve, ointment, powder, liquid, granules, candle, vapor, beads and the like. Certain non-limiting examples of ternary base formulations are shown in Table 4.

TABLE 4

Repellent Formulations

| Component (CAS Reg. No) | Weight percent of Component Base Formulation 5 |
|---|---|
| Putrescent Whole Egg Solids (51609-52-0) | 0.01-15 |
| Cinnamon Oil (8015-91-6) | 0.05-10 |
| Clove Oil (8000-34-8) | 0.05-10 |
| Other ingredients | 43-97.4 |

Repellent formulations of the present invention may comprise a base formulation which includes geraniol oil and rosemary oil. In one embodiment, the base formulation comprises geraniol oil from 0.05 to 30 percent by weight and rosemary oil from 0.07-8.5 percent by weight, in combination with one or more mint oils from 0.05 to 15 percent by weight and castor oil from 0.2 to 55 percent by weight. A further embodiment may comprise geraniol oil from 2 to 30 percent by weight in combination with rosemary oil from 0.5 to 6 percent by weight, mint oil from 0.1 to 10 percent by weight, castor oil from 0.3 to 20 percent by weight and other ingredients added in the formulation may be selected from, but not limited to, a thickener, a binder, a gelling agent, a solvent and a vegetable oil.

In another embodiment, the base formulation comprises geraniol oil from 0.05 to 30 percent by weight and rosemary oil from 0.07-8.5 percent by weight, in combination with one or more mint oils from 0.05 to 15 percent by weight, castor oil from 0.2 to 55 percent by weight and cinnamon oil from 0.05 to 10 percent by weight. A further embodiment may comprise geraniol oil from 2 to 30 percent by weight in combination with rosemary oil from 0.5 to 6 percent by weight, mint oil from 0.1 to 10 percent by weight, castor oil from 0.3 to 20 percent by weight, cinnamon oil from 0.5 to 8 percent by weight and other ingredients added in the formulation may be selected from, but not limited to, a thickener, a binder, a gelling agent, a solvent and a vegetable oil. Certain nonlimiting examples of base formulations comprising geraniol oil and rosemary oil are shown in Table 5.

TABLE 5

Geraniol Oil and Rosemary Oil Base Repellent Formulations

| Component (CAS Reg. No) | Weight percent of Component Base Formulation 6 | Weight percent of Component Base Formulation 7 |
|---|---|---|
| Geraniol oil (106-24-1) | 0.05-30 | 0.05-.30 |
| Rosemary oil (8000-25-7) | 0.07-8.5 | 0.07-8.5 |
| Mint oil | 0.05-15 | 0.05-15 |
| Castor oil (8001-79-4) | 0.2-55 | 0.2-55 |
| Cinnamon oil (8007-80-5) | — | 0.05-10 |
| Other ingredients | 11.5-99.63 | 1.5-99.58 |

"Other ingredients" which may be added to the base formulations include, but are not limited to, ingredients which are disclosed herein or known to those skilled in the art. Other ingredients may also include milk, bitrex, thiram, methyl ammonium saccharide, thymol, garlic, garlic powder, garlic oil, capsaicin, hot pepper, white pepper, oil of black pepper, piperine, chemically formulated pepper, predator urines (large cat and carnivores), chemically formulated predator urines, urea, naphthalene (moth balls), pyrethrine, blood, blood meal, bone meal, sulfurous emitting items (eggs, sulfur, meats, etc), denatonium benzoate, ammonium of fatty acids, butyl mercaptan, clove, fish oil, onion, ammonia, mineral oil, orange oil, kelp (seaweed), nut shells such as, but not limited to, walnut shells, peanut shells, whole eggs, powdered eggs, putrescent eggs, egg whites, egg yolks, rotten eggs, rosemary, wintergreen, 2-propenoic acid, potassium salt, 2-propeniamide, 2 phenethyl propionate, acetic acid, vinegar, latex, animal glue, clay, Fuller's earth, formaldehyde, stickers like nufilm p and others in the series, and thyme.

It should be understood that the base formulations in Tables 1, 2, 3, 4 and 5 may be formulated as liquid, solid or gel form and may be diluted or formulated as concentrates in liquid, solid or gel form.

As used herein the term "aqueous" means similar to or containing or dissolved in water, e.g., an aqueous solution. A "slurry" according to the present invention is a suspension of predominantly insoluble particles, usually in water. A "mixture" according to the present invention is a substance consisting of two or more substances mixed together.

Formulations may also be in the form of solid mixtures, whether in bulk, small particulate or dust form. As used herein, the term "particulate" means any solid in a subdivided state. Particulates are larger than dusts however dusts may be considered particulates. Particulates may be homogenous or heterogeneous. They may be granules or particles, organic or inorganic.

The compositions of the present invention may also be applied to a surface or substrate. As used herein a "surface" is the outer boundary of an object, a material layer constituting or resembling such a boundary or the extended two-dimensional outer boundary of a three-dimensional object, while a "substrate" is any stratum or layer lying underneath another. A substrate need not be laminar and may also comprise a solid carrier or particulate.

The compositions of the present invention may be optionally mixed with carrier vehicle assistants, e.g. conventional surface-active agents, including emulsifying agents and/or dispersing agents. Further, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the repellent composition and the ability of the agent to facilitate the dispersion of the repellent compositions. Non-ionic, anionic, amphoteric, or cationic dispersing and emulsifying agents may be employed.

Liquid repellent compositions may be prepared by dispersing a repellent concentrate formulation of the present invention in water or suitable solvent.

The concentrated formulation may be an aqueous solution, slurry or mixture (wet or dry), comprising multiple components that may be adjusted either in the preparation of the concentrate or during the final dilution step prior to use or application.

Table 6 illustrates geraniol repellent concentrate formulations (compositions) of the present invention. The range of the amount of each component (in % by weight) is given. Where available and for reference, CAS Registry Numbers are provided. As used herein "CAS Registry Number" means the identifier assigned to a particular substance by Chemical Abstracts Service, a division of the American Chemical Society. The CAS Registry Number is not meant to be limiting and, where no number is provided, is not meant to suggest none exists.

TABLE 6

Geraniol Repellent Concentrate Formulations

| Component (CAS Reg.) No) | Weight percent of Component | | | | | | |
|---|---|---|---|---|---|---|---|
| | Formulation A | Formulation B | Formulation C | Formulation D | Formulation E | Formulation F | Formulation G |
| Geraniol oil (106-24-1) | 0.05-30 | 3-25 | 5-20 | 0.05-30 | 0.05-30 | 0.05-30 | 0.05-30 |
| Rosemary oil (8000-25-7) | — | — | — | 0.07-8.5 | 0.07-8.5 | — | — |
| Mint oil | 0.05-15 | 0.1-8.5 | 0.3-5.5 | 0.05-15 | 0.05-15 | 0.05-15 | 0.05-15 |
| Cinnamon oil (8007-80-5) | — | — | — | — | 0.05-10 | — | 0.05-10 |
| Castor oil (8001-79-4) | 0.2-55 | 0.75-20.5 | 2.1-7.2 | 0.2-55 | 0.2-55 | 0.2-55 | — |
| Sodium lauryl sulfate (151-21-3) | 0.002-9.3 | 0.005-6.5 | 0.01-1 | 0.002-9.3 | — | 0.002-9.3 | — |
| Kaolin clay (1332-58-7) | 0.01-10 | 0.03-5 | 0.05-2 | 0.01-10 | 0.01-10 | — | — |
| Xanthan Gum (11138-66-2) | 0.1-7.5 | 0.5-4.5 | 0.1-2.3 | 0.1-7.5 | 0.1-7.5 | 0.1-7.5 | — |
| Calcium carbonate (471-34-1) | — | — | — | 0.1-10 | — | — | — |
| Clove oil (8000-34-8) | — | — | — | — | — | — | 0.05-10 |
| Eugenol (97-53-0) | — | — | — | — | — | — | 0.05-10 |
| Water (7732-18-5) | 55-95.6 | 60-93.3 | 65-91 | 55-95.6 | 55-95.6 | 55-95.6 | 55-95.6 |

Table 7 illustrates rosemary and putrescent whole egg solid repellent concentrate formulations (compositions) of the present invention.

TABLE 7

Repellent Concentrate Formulations

| Component (CAS Reg.) No) | Weight percent of Component | | | | | |
|---|---|---|---|---|---|---|
| | Formulation H | Formulation I | Formulation J | Formulation K | Formulation L | Formulation M |
| Rosemary oil (8000-25-7) | — | 0.05-30 | — | — | 0.05-30 | — |
| Putrescent Whole Egg Solids (51609-52-0) | 0.01-15 | 0.01-15 | 0.01-15 | 0.01-15 | 0.01-15 | — |
| Mint oil | — | 0.05-15 | — | — | 0.05-15 | — |

TABLE 7-continued

Repellent Concentrate Formulations

| Component (CAS Reg.) No) | Weight percent of Component | | | | | |
|---|---|---|---|---|---|---|
| | Formulation H | Formulation I | Formulation J | Formulation K | Formulation L | Formulation M |
| Cinnamon oil (8007-80-5) | 0.05-10 | 0.05-10 | 0.05-10 | 0.05-10 | 0.05-10 | 0.05-10 |
| Clove oil (8000-34-8) | 0.05-10 | — | 0.05-10 | 0.05-10 | — | 0.05-10 |
| Potassium Sorbate (24634-61-5) | 0.001-5 | 0.001-5 | 0.001-5 | 0.001-5 | 0.001-5 | — |
| Kaolin clay (1332-58-7) | — | 0.01-10 | — | 0.01-10 | 0.01-10 | — |
| Vinegar | 0.1-5 | 0.1-5 | 0.1-5 | 0.1-5 | 0.1-5 | — |
| Sodium Chloride (7647-14-5) | 0.01-5 | | 0.01-5 | 0.01-5 | 0.01-5 | — |
| Xanthan Gum (11138-66-2) | 0.01-7.5 | 0.01-7.5 | 0.01-7.5 | 0.01-7.5 | 0.01-7.5 | — |
| Eugenol (97-53-0) | — | — | — | — | — | 0.05-10 |
| Sodium lauryl sulfate (151-21-3) | — | — | — | — | — | 0.002-9.3 |
| Water (7732-18-5) | 55-95.6 | 55-95.6 | 55-95.6 | 55-95.6 | 55-95.6 | 55-95.6 |

In one embodiment, the repellent formulation may comprise about 0.5-1% by weight putrescent whole egg solid, about 0.1-0.5% by weight cinnamon oil, about 0.05-0.5% by weight clove oil, about 0.01-0.1% by weight potassium sorbate, about 0.1-0.5% sodium chloride, about 0.1-1% by weight vinegar, about 0.1-0.5% by weight xanthan gum and about 90-99% by weight water.

In one embodiment, the repellent formulation may comprise about 0.76% by weight putrescent whole egg solid, about 0.22% by weight cinnamon oil, about 0.14% by weight clove oil, about 0.06% by weight potassium sorbate, about 0.30% sodium chloride, about 0.50% by weight vinegar, about 0.17% by weight xanthan gum and about 97.32% by weight water.

In one embodiment, the repellent formulation may comprise about 1-5% by weight rosemary oil, about 1-5% by weight mint oil, about 0.1-1% by weight cinnamon oil, about 1-5% by weight putrescent whole egg solids, about 0.1-1% by weight kaolin, about 0.01-0.1% by weight potassium sorbate, about 0.1-0.5% sodium chloride, about 0.1-1% by weight vinegar, about 0.1-0.5% by weight xanthan gum and about 90-99% by weight water.

In one embodiment, the repellent formulation may comprise about 1.68% by weight rosemary oil, about 1.68% by weight mint oil, about 0.42% by weight cinnamon oil, about 1.53% by weight putrescent whole egg solids, about 0.53% by weight kaolin, about 0.05% by weight potassium sorbate, about 0.33% sodium chloride, about 0.50% by weight vinegar, about 0.50% by weight xanthan gum and about 92.78% by weight water.

In one embodiment, the repellent formulation may comprise about 1-5% by weight geraniol, about 1-5% by weight mint oil, about 1-5% cinnamon oil, about 1-5% by weight clove oil, about 1-5% by weight eugenol, and about 50-99% by weight water. In a further embodiment, the repellent composition may comprise walnut shells.

In one embodiment, the repellent formulation may comprise about 1-10% by weight putrescent whole egg solids, about 1-5% by weight cinnamon oil, about 1-5% by weight clove oil, about 0.01-0.1% by weight potassium sorbate, about 0.5-1% sodium chloride, about 0.5-5% by weight vinegar, about 0.1-0.8% by weight xanthan gum and about 80-95% by weight water.

In one embodiment, the repellent formulation may comprise about 0.1-1% by weight rosemary oil, about 0.1-1% by weight mint oil, about 0.1-1% by weight cinnamon oil, about 0.1-1% by weight putrescent whole egg solids, about 0.01-0.1% by weight kaolin, about 0.01-0.1% by weight potassium sorbate, about 0.1-0.5% by weight sodium chloride, about 0.01-0.1% by weight vinegar, about 0.01-0.05% by weight xanthan gum, and about 90-99% by weight water. In a further embodiment, the repellent composition may comprise walnut shells.

In one embodiment, the repellent formulation may comprise about 0.56% by weight rosemary oil, about 0.37% by weight mint oil, about 0.44% by weight cinnamon oil, about 0.21% by weight putrescent whole egg solids, about 0.02% by weight kaolin, about 0.03% by weight potassium sorbate, about 0.20% by weight sodium chloride, about 0.04% by weight vinegar, about 0.01% by weight xanthan gum, about 98.10% by weight walnut shells and about 0.02% by weight water.

In one embodiment, the repellent composition may comprise about 1-10% by weight geraniol, about 1-5% by weight of mint oil, about 40-55% by weight castor oil, about 1-5% by weight sodium lauryl sulfate, about 0.01-0.1% by weight xanthan gum, and about 30-50% by weight water.

In one embodiment, the repellent composition may comprise about 5.62% by weight geraniol, about 2.60% by weight of mint oil, about 46.66% by weight castor oil, about 2% by weight sodium lauryl sulfate, about 0.08% by weight xanthan gum, and about 43.04% by weight water.

In one embodiment, the repellent composition may comprise about 7.5% by weight geraniol, about 0.54% by weight of mint oil, about 3.8% by weight castor oil, about 0.03% by weight sodium lauryl sulfate, about 0.13% by weight xanthan gum, and about 88% by weight water.

In some embodiments, repellent formulations are prepared to repel mammals (e.g., rodents), birds, and insects from seeds (e.g., vegetable seeds, grass seeds, flower seeds, bird seeds, sunflower seeds, and plant seeds), grains, and nuts using the repellent formulations in the following Table.

TABLE 8

Repellent formulations

| Component (CAS Registration Number) | Weight percent of component | | | |
|---|---|---|---|---|
| | Formulation N | Formulation O | Formulation P | Formulation Q |
| Geraniol oil (106-24-1) | 5.0-7.5 | 15-22.5 | 2.5-5.0 | 5.5 |
| Castor oil (8001-79-4) | 2.0-5.0 | 6-12 | 1.0-2.0 | 2.5 |
| Peppermint oil (8006-90-4) | 6.0-9.0 | 18-24 | 2.0-5.5 | 6.6 |
| Rosemary oil (8000-25-7) | 2.0-8.0 | 12-24 | 2.0-3.0 | 4.5 |
| Cinnamon oil (8007-80-5) | 4.0-8.0 | 12-24 | 2.0-3.0 | 4.9 |
| Xanthan gum (11138-66-2) | 0.10-0.50 | 0.3-0.9 | 0.05-0.5 | 0.15 |
| Kaolin clay (1332-58-7) | 0.9-2.0 | 3.0-6.0 | 0.45-1.0 | 1.1 |
| Water | 60-80 | | 80-90 | 74.75 |

In some cases, the present invention provides repellent seed compositions. As used herein, the term "repellent seed composition" refers to seed products formed from the combination of seeds with repellent formulations. Some repellent seed compositions may be prepared by combining any of repellent formulations N-O with seeds at ratio of about 10 g of formulation to about 1 lb of seeds. In some cases, seeds may be treated with about 0.01 g to about 2.0 g, from about 0.02 g to about 5.0 g, from about 0.05 g to about 3 g, from about 1.0 g to about 5.0 g, from about 1.5 g to about 7.5 g, from about 2.0 g to about 10 g, from about 2.5 g to about 15 g, from about 5 g to about 20 g, from about 7.5 g to about 15 g, from about 8.0 g to about 12.0 g, from about 10 g to about 50 g, from about 12 g to about 24 g, from about 15 g to about 30 g, from about 20 g to about 40 g, from about 30 g to about 60 g, or from about 40 g to about 80 g of formulation N, O, P, or Q per pound of seeds. Treated seeds may further be allowed to dry for storage or other applications.

In some embodiments, the present invention provides granular repellent compositions. As used herein, the term "granular repellent composition" refers to products formed by combining granular materials (e.g., crushed walnut shells) with concentrated repellent formulations. In the preparation of granular rodent repellent compositions, repellent concentrates provided in the following Table may be combined with walnut shells (or other granular carrier) and used for repelling rodents (e.g., mice, rabbits, squirrels, and groundhogs). The final percentage in the granular mixture presented in the Table is based on combining 19.5 g of formulation C3 with 1 pound of a granular carrier (e.g., crushed walnut shells). In the final mixture, water is evaporated in the process of mixing with the granular carrier.

TABLE 9

Concentrate formulations for granular application

| Component (CAS Registration Number) | Weight percent of component | | | Final % in granular mixture with C3 |
|---|---|---|---|---|
| | Formulation C1 | Formulation C2 | Formulation C3 | |
| Geraniol oil (106-24-1) | 0.05-30 | 3-10 | 5.75 | 0.25 |
| Castor oil (8001-79-4) | 0.2-55 | 20-35 | 20 | 0.86 |
| Peppermint oil (8006-90-4) | 10-25 | 15-20 | 16.49 | 0.7 |
| Rosemary oil (8000-25-7) | 15-25 | 17.5-22.5 | 21.57 | 0.93 |
| Cinnamon oil (8007-80-5) | 5-20 | 10-15 | 10.8 | 0.46 |
| Xanthan gum (11138-66-2) | 0.01-5 | 0.1-2.3 | 0.23 | 0.01 |
| Kaolin clay (1332-58-7) | 0.01-5 | 0.05-2 | 1.1 | 0.05 |
| Water | 0-69.73 | 0-65.65 | 24.06 | |
| Walnut shells | | | | 96.74 |

In some cases, concentrated formulations are combined with granular material (or other carriers) at a concentration of from about 0.5 g/lb carrier to about 2 g/lb carrier, from about 1 g/lb carrier to about 5 g/lb carrier, from about 2 g/lb carrier to about 10 g/lb carrier, from about 5 g/lb carrier to about 20 g/lb carrier, from about 10 g/lb carrier to about 30 g/lb carrier, from about 15 g/lb carrier to about 45 g/lb carrier, from about 20 g/lb carrier to about 60 g/lb carrier, from about 30 g/lb carrier to about 90 g/lb carrier, from about 50 g/lb carrier to about 150 g/lb carrier, from about 100 g/lb carrier to about 300 g/lb carrier, from about 200 g/lb carrier to about 500 g/lb carrier, from about 400 g/lb carrier to about 1 kg/lb carrier, or from about 500 g/lb carrier to about 2 kg/lb carrier.

In some embodiments, granular repellent compositions are used to repel pests from an area or surface. In some cases, such areas include pest habitats, nests, or boroughs. According to some embodiments, granular repellent compositions are used to repel rodents from outdoor areas including, but not limited to, yards, trails, gardens, fields or forests. In one embodiments, granular repellent compositions are placed in and around pest habitats (e.g., a rodent hole or borough).

Carriers

In addition to the components listed in the Tables above, the repellent compositions and formulations of the present invention may contain one or more carriers or carrier vehicles. As used herein a "carrier" is a substance that transmits, serves, or aids in transmission or acts as the medium for transmission. Carriers may be liquid or solid. They are most often inert but may be active ingredients.

Examples of conventional carrier vehicles include, but are not limited to, aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g., vermiculite, alumina, silica, chalk, i.e. calcium carbonate, talc, attapulgite, montmorillonite, kieselguhr, etc.) and ground synthetic minerals (e.g. highly dispersed silicic acid, silicates, e.g., alkali silicates, etc.).

The repellent compositions of the present invention may be admixtures with finely divided solids such as talc, attapulgite clay, kieselguhr, pyrophyllite, chalk, diatomaceous earth, vermiculite, calcium phosphates, calcium and magnesium carbonates, sulfur, flours, and other organic and inorganic solids which act as carriers. These finely divided solids, or dusts, preferably have an average particle size of less than about 50 microns. A typical dust formulation useful for controlling pests contains 1 part of pesticidal composition and 99 parts of diatomaceous earth or vermiculite. Granules may comprise porous or nonporous particles. The granule particles are relatively large, a diameter of about 400-2500 microns typically. The particles are either impregnated or coated with the inventive repellent compositions from solution. Granules generally contain 0.05-15%, preferably 0.5-5%, active ingredient as the pesticidally-effective amount. Thus, the repellent compositions of the present invention can be formulated with any of the following solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs, tobacco stalks and other natural cast off products that may or may not be a by-product of manufacturing or harvest such as walnut or nut shells or egg shells.

Surface-Active Agents

It may also be necessary to include one or more surface active agents. Surface-active agents, (i.e., conventional carrier vehicle assistants) that may be employed with the present invention include, without limitation, emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, and especially alkyl arylpolyglycol ethers, magnesium stearate, sodium oleate, etc.); and/or dispersing agents such as lignin, sulfite waste liquors, methyl cellulose, etc.

Thickeners

One or more thickeners or thickening agents may be added to the compositions of the present invention. "Thickeners" are substances which, when added to a mixture (aqueous or otherwise), increase its viscosity without substantially modifying its other properties. Thickeners may be used to ensure uniform consistency. A starch, thickener, or gelling agent may also be used to alter the consistence of the repellent compositions of the present invention. Agar, corn starch, potato starch and guar gum or the like, may be used. These agents can also be added to keep the ingredients in suspension. Typically thickeners are added at about 0.1 to 5% of the total composition.

Preservatives

Preservatives may be added to the compositions and formulations of the present invention. As used herein a "preservative" is any substance or compound that is added to protect against decay, decomposition or spoilage. Means of preservation may also be utilized. Preservatives may be natural or synthetic. They may be antimicrobial preservatives, which inhibit the growth of bacteria or fungi, including mold, or antioxidants such as oxygen absorbers, which inhibit the oxidation of food constituents. Common antimicrobial preservatives include calcium propionate, sodium nitrate, sodium nitrite, sulfites (sulfur dioxide, sodium bisulfite, potassium hydrogen sulfite, etc.) and disodium EDTA. Antioxidants include BHA and BHT. Other preservatives include formaldehyde (usually in solution), glutaraldehyde (kills insects), ethanol and methylchloroisothiazolinone. A preservative, such as potassium sorbate can be added to the compositions or formulations. Typically, preservatives appear in the compositions at between 0.03 to 3% by weight percent.

Other Components

Optional components such as one or more dilute acids, other naturally occurring insecticides, sodium chloride and potassium soaps increase the range of activity of the base repellent composition with regard to the number of animal species repelled and the duration of the repulsive effect. Therefore, these may be added in suitable weight percent amounts. Other possible additives are perfumes, mineral or vegetable, optionally modified oils, waxes and nutrients (including trace nutrients), such as salts of iron, manganese, boron, copper, cobalt, molybdenum and zinc.

Other Aromatics

The addition of cedar oil to the composition enhances the effectiveness of the composition as an animal repellent. It also adds ability to repel insects and kill mosquito larvae in water. Cedar oil may be added at between 0.03% and 10%. It may be added between 1% and 5%, between 2% and 4% or between 5% and 10%.

Cinnamon oil, clove oil and/or eugenol may be added to the composition enhances the effectiveness of the composition as an animal repellent. Cinnamon oil, clove oil and/or eugenol may be added at between 0.05% and 10%. It may be added between 1% and 5% or between 5% and 10%.

Camphor is a waxy, white or transparent solid with a strong, aromatic odor. It is a terpenoid with the chemical formula $C_{10}H_{16}O$. It is found in wood of the camphor laurel (*Cinnamomum camphora*), a large evergreen tree found in Asia (particularly in Borneo and Taiwan). It also occurs in some other related trees in the laurel family, notably *Ocotea usambarensis*. Camphor has been used as an insect repellent and may be added to the repellent compositions of the present invention in amounts of (by weigh percent) 0.01% to 15%. It may be added between 1% and 5%, between 2% and 4% or between 5% and 10%.

Pyrethrin

An additional optional component is a natural insecticide such pyrethrin. The pyrethrins are a pair of natural organic compounds that have potent insecticidal activity. Pyrethrin I and pyrethrin II are structurally related esters with a cyclopropane core. They differ by the oxidation state of one carbon and exist as viscous liquids.

The pyrethrins are contained in the seed cases of the perennial plant pyrethrum (*Chrysanthemum cinerariaefolium*), which is grown commercially to supply the insecticide.

When present in amounts not fatal to insects in the present formulations, they have an insect repellent effect. They are harmful to fish, but are far less toxic to mammals and birds than many synthetic insecticides. Pyrethrins are non-persistent, biodegradable, break down easily on exposure to light or oxygen and are considered to be among the safest insecticides for use around food.

Among the synthetic analogs of pyrethrin is permethrin. It is a member of the pyrethroid family and functions as a neurotoxin, by prolonging sodium channel activation and is the preferred synthetic pyrethroid although other members may be utilized in the present invention. The pyrethrins may be added at between 0.001% and 10%. It may be added between 1% and 5%, between 2% and 4% or between 5% and 10%.

Adjuvants

According to the present invention one or more adjuvants may be added to the repellent compositions. As used herein an "adjuvant" is a substance that aids, assists or improves one or more properties or activities of another substance.

Adjuvant categories include, but are not limited to, wetting agents and/or spreading agents (surfactants), sticking agents, adhesives, foam retardants, buffers, acidifiers, colorants, stabilizers and waterproofing agents.

Wetting/Spreading agents

A sprayed drop comprising an active agent, e.g., a repellent composition must be able to wet the surface and spread out or cover an area to perform its intended function. In some situations, a wetting agent (also known as a spreading agent or surfactant) is necessary for good coverage. A wetting agent/surfactant reduces the surface tension of the water on the surface of the spray drop and by reducing the interfacial tension between the spray drop and surface. This requires a surfactant that will preferentially aggregate at these surfaces. Surfactants wet and disperse particles of active ingredient(s) in the concentrate or upon dilution prior to spraying, and wet the target surface with the pesticide spray to achieve more effective coverage of the target. Concentrated multipurpose wetting agents typically contain a blend of bio-degradable, non-ionic surfactants and an emulsified silicone type antifoam preparation. This action provides uniform wetting and coverage. Exemplary surfactants include amphoteric/zwitterionic surfactants; anionic surfactants; nonionic surfactants; cationic surfactants. Amphoteric surfactants useful in the invention can be described as a surface active agent containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants can be described as surface active agents having a positive and negative charge in the same molecule which molecule is zwitterionic at all pH's. Zwitterionic surfactants can be best illustrated by betaines and sultaines. The zwitterionic compounds generally contain a quaternary ammonium, quaternary phosphonium or a tertiary sulfonium moiety. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate. Examples of suitable amphoteric and zwitterionic surfactants include the alkali metal, alkaline earth metal, ammonium or substituted ammonium salts of alkyl amphocarboxyglycinates and alkyl amphocarboxypropionates, alkyl amphodipropionates, alkyl monoacetate, alkyl diacetates, alkyl amphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates. Anionic surfactants which may be used in the present invention are those surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants.

Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water soluble salts and mixtures of salts of alkyl benzene sulfonates having between 8 and 22 carbon atoms in the allyl group, alkyl ether sulfates having between about 8 and about 22 carbon atoms in the alkyl group and about 2 to about 9 moles ethylene oxide in the ether group. Other anionic surfactants that can be mentioned include alkyl sulfosuccinates, alkyl ether sulfosuccinates, olefin sulfonates, alkyl sarcosinates, alkyl monoglyceride sulfates and ether sulfates, alkyl ether carboxylates, paraffinic sulfonates, mono and dialkyl phosphate esters and ethoxylated derivatives, acyl methyl taurates, fatty acid soaps, collagen hydrosylate derivatives, sulfoacetates, acyl lactates, aryloxide disulfonates, sulfosuccinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or propylene oxide (PO), preferably EO. Specific anionic surfactants which may be selected include linear alkyl benzene sulfonates such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

The nonionic surfactant(s) may be any of the known nonionic surfactants which are generally selected on the basis of compatibility, effectiveness and economy. Examples of useful nonionic surfactants include condensates of ethylene oxide with a hydrophobic moiety. The surfactants include the ethoxylated primary or secondary aliphatic alcohols having from about 8 to about 24 carbon atoms, in either straight or branch chain configuration, with from about 2 to about 40, and preferably between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide. Many cationic surfactants are known in the art and almost any cationic surfactant having at least one long chain allyl group of about 10 to 24 carbon atoms is suitable for optional use in the present invention.

Sticking Agents

A sticking agent can perform three types of functions. It can increase the adhesion or "stickiness" of solid particles that otherwise might be easily dislodged from a surface. It can also reduce evaporation of the formulation. The third function can be to provide a waterproof coating. If the sticking agent is not water soluble, it can provide a degree of protection from this form of loss.

Many of the sticking agents contain surfactants as their principal functioning agent and give both a sticking action and a wetter-spreader action. These will perform the first two functions quite well. But since the surfactants that provide wetter-spreader action must be somewhat water soluble, they may not provide good protection from rain. This will be provided by products that contain natural resins (rosin), or other waterproofing agents. Sticking-spreaders can be made of many different components, organic or inorganic. Some are silicone-based surfactants, oils, emulsifiers and buffering agents, while others may contain combinations such as fish oil or fatty acid soaps or emulsified soybean oil. Sticking agents include tackifiers. Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

Adhesives

Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrates.

Foam Retardants

Some formulations will create foam in spray tanks as a result of both the surfactants used in the concentrate formulation and the type of spray tank agitation. This foam can be reduced or eliminated by a small amount of foam inhibitor.

Oil based defoamers have an oil carrier. The oil might be mineral oil, vegetable oil, white oil or any other oil that is insoluble in the foaming medium, except silicone oil. An oil based defoamer also contains a wax and/or hydrophobic silica to boost the performance. Typical waxes are ethylene bis stearamide (EBS), paraffinic waxes, ester waxes and fatty alcohol waxes. These products might also have surfactants to improve emulsification and spreading in the foaming medium.

Water based defoamers are different types of oils and waxes dispersed in a water base. The oils are often white oils or vegetable oils and the waxes are long chain fatty alcohol, fatty acid soaps or esters. These are normally best as deaerators, which mean they are best at releasing entrained air.

Silicone-based defoamers have a silicone compound as the active component. These might be delivered as oil or a water based emulsion. The silicone compound consists of an hydrophobic silica dispersed in a silicone oil. Emulsifiers are added to ensure that the silicone spreads fast and well in the foaming medium. The silicone compound might also contain silicone glycols and other modified silicone fluids.

EO/PO based defoamers contain polyethylene glycol and polypropylene glycol copolymers. They are delivered as oils, water solutions, or water based emulsions. EO/PO copolymers normally have good dispersing properties and are often well suited when deposit problems are an issue.

Alkyl polyacrylates are suitable for use as defoamers in non-aqueous systems where air release is more important than the breakdown of surface foam. These defoamers are often delivered in a solvent carrier like petroleum distillates.

Foam retardants or defoamers may be used in the compositions of the present invention between 0.5% and 10% by weight.

Buffers

Some water used for diluting formulations is alkaline (high pH). If the pH is sufficiently high and the pesticide is subject to degradation by alkaline hydrolysis, it may be necessary to lower the pH of the mix water to a pH in the range of 3 to 7, preferably 3.75 to 4.25. Buffers containing phosphoric acid or a salt of phosphoric acid, will lower the pH of the water and tend to stabilize the pH at an acceptable value. The efficacy of the buffer depends on its concentration of phosphoric acid and the degree of alkalinity or "hardness" of the mixing water that is being neutralized. The more alkaline the water, the greater the amount of buffer required.

Some buffers have sufficient surfactant present to also perform as wetter-spreaders. The concentration of surfactant and phosphoric acid are usually lumped together and it is not possible to determine the concentration of either and thus predict their efficacy. A useful range for phosphoric acid buffer concentration is from about 2 to 10%.

Acidifiers

Buffers that acidify alkaline spray waters increase the effectiveness. Buffers can help increase the residual life of the formulation about two-fold and can result in reducing the number of spray applications per season. Muriatic acid, Buffer-X or vinegar are not effective for this purpose. The duration and scope of effectiveness of the present invention may also be increased by adding a dilute acid to the composition, especially acetic acid, which may be in the form of vinegar, preferably white distilled vinegar having an acid content of between 3.5 and 5% acetic acid. Dilute acid may be added to the composition of the present invention between about 0.01% to about 5% by weight.

Colorants

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Colorants are advantageous when it is important for the repellent compositions or formulations when applied to blend in, or be less detectable in the environment applied. This advantage is sometimes aesthetic but can serve a functional role where pests are likely to either be attracted or repelled based on color.

The use of these adjuvants provides a variety of benefits including improved coverage of the spray both in the soil and on plant surfaces, increased retention on surfaces, reduced evaporation, reduced foaming problems in the tank, easier sprayer cleaning and lubrication of pump and sprayer nozzles.

Stabilizers

Stabilizers, such as low-temperature stabilizers, preservatives, antioxidants, light stabilizers or other agents which improve chemical and/or physical stability may also be present. Stabilizers are useful to inhibit the reaction between two or more other chemicals. They can also inhibit separation of suspensions, emulsions, and foams.

Applications and Methods

The repellent compositions may be applied to any surface or substrate by any convenient method. It is expected that spraying will be the application method of choice in most circumstances where a liquid formulation is used. For example, an aircraft may be used to spray the liquid formulation over crops or fields. Other methods of application contemplated include, but are not limited to, painting, brushing, mopping, spreading, banding, broadcasting, side-dressing, coating, rolling, bathing, dipping, immersing, soaking, adhering, sticking, spraying, rubbing, wiping, impregnating, injecting, embedding, sealing, stippling, dotting, dabbing, stenciling, stamping, layering, spackling, sprinkling, aerosolizing, misting, dusting, vaporizing, pouring and the like.

Methods of application may also be indirect. For example, containers or vessels holding an amount of a repellent composition may be placed in an area to be treated with dispersion of the composition being effected by forces of nature, e.g., wind, rain, current, radiant heat. Air spraying apparatuses may be employed such as those disclosed in U.S. Pat. No.

4,172,557, the contents of which are incorporated herein in its entirety. Dispersion may also be effected from a container whereby dispersion is activated by movement such as a motion sensor. Aerosol dispersion is particularly amenable to automatic release via motion detection. Indirect methods also include the use of mechanical devices to effect the applications listed herein. For example, timed spreaders or broadcasters may be set up in predetermined areas in order to apply or disperse the repellents to a surface, area or substrate in a temporal fashion, e.g., automated application. Triggering of timed spreaders or timed distribution may be predetermined or may occur on signal either remotely initiated or initiated as part of a timed sequence after a detection event. For example, application of the repellent may occur at a time after trigger by a motion detector of the presence of a pest.

Indirect methods also include the use of devices such as those disclosed in U.S. Pat. No. 6,192,621, the contents of which are incorporated herein by reference in their entirety. In this application, the animal repellents, alone or in combination with other agents or repellents are installed in the animal control device capable of repelling or attracting pests to any area in which the device is placed.

In some embodiments, the present invention provides methods of storing or using seeds (e.g., vegetable seeds, grass seeds, flower seeds, bird seeds, sunflower seeds, plant seeds), that prevents pest visitation and/or consumption of such seeds. Such methods comprise the treatment of seeds with a repellent formulation of the invention to form a repellent seed composition. In some cases, seeds are further dried after treatment. Repellent seed compositions may be stored for a period of from about a day to about a week, from about 2 days to about 2 weeks, from about a week to about 4 weeks, from about 2 weeks to about 10 weeks, from about 5 weeks to about 50 weeks, from about 10 weeks to about 100 weeks, or from about 1 year to about 5 years with reduced or eliminated seed consumption by pests (e.g., rodents and birds). In some embodiments, such methods include the use of grass seeds. Grass seeds may be treated with repellent formulations and applied to areas for growing grass. Grass seeds comprising repellent seed compositions may be resistant to consumption by pests (e.g., rodents and birds).

Pest Management Systems

The present invention provides for a pest control management system or "pest management system" or "PMS" which are functional to control pest populations either by preventing ingress or egress or by attracting pests for containment and/or relocation as well as for extermination. In this system, a repellent (or attractant) formulation is incorporated into, used with a device which resembles, is disguised as, or is already an integral part of its environment. The system may also be used in conjunction with commercially available attractants and as such incorporate commercial or non-commercial baits, abatement systems, traps or bait boxes. The advantages of such a disguised trapping system include ease of use and a more acceptable presence. As such, they would be superior to unattractive traps and consequently be used more often which would, by definition, result in more trapped pests.

The repellent and/or attractant compositions useful in conjunction with the PMSs of the present invention include any of those of standard use in the art. It is of special interest to employ repellents and attractants which are generally accepted as safe (GRAS). Examples of such compositions are disclosed in, for example, commonly-owned International PCT filing PCT/US2011/031901 filed Apr. 27, 2011, the contents of which are incorporated herein by reference in their entirety.

Multiple pest management systems may be combined.

The body of the system may be the only portion which is disguised. The variable housing may be the only portion of the system which is disguised. The composition housing may be the only portion of the system which is disguised.

In one embodiment, the systems of the invention may be an object that is configured to resemble and/or disguised as an item that blends and/or integrates into its environment. As used herein, "configured to resemble" and "disguised as" refers to an object that is made to appear as, is similar to, takes on a false appearance of, is camouflaged as, and the like, that may occur in the environment in which the object is placed. As used herein, "blends" and "integrates into" refers to the ability of an object to appear natural or normal or native, incorporate, merge, mingle, assimilate, combine, coordinate, unite, and the like, with its environment.

Devices and means for application of the formulations as pest management systems include, but are not limited to, plant pots, plant pot saucers, vases, door jams, buckets, cans, pans, glass bottles, plastic bottles, used household container items, food container, any empty container, food items, articles of clothing such as socks, stockings, and the like, cardboard or degradable boxes, paper, newspaper, books, deck of cards, logs, rocks, outdoor equipment such as tents, tent stakes and the like.

A further embodiment is a pest management system which includes a signal to alert that a pest has been captured in or come close to the device. "Signal" as used herein refers to a sign, indication, indicator, gesture or object that conveys a notice to a person. A "signal" can include, but is not limited to, a flag, sound, smell (odor), motion, blinking light and the like. For example, a device may be a container configured to resemble a log with a compartment inside the log housing an attractant formulation and an opening to allow a pest to enter the device. Once a pest enters the device, the pest triggers a mechanism that closes the opening and the same or another mechanism causes a signal, such as a flag, to rise out of the device.

Formulations which function in a timed-release, extended release and/or controlled release manner are also contemplated by the devices of the present invention. As used herein "time release" or "timed release" refers to a composition which exerts its effect over a period of time. The period of time may be measured in days, weeks or months. "Extended release" refers to compositions which have been formulated to exert their effects over an extended period of time. Extended release compositions are by definition time-release compositions. Extended release compositions are those which exert their effects over a period of time greater than one week. As used herein "controlled release" means the liberation of the repellent composition of the invention into the intended environment in a regular manner or pattern. Controlled release formulations are often timed release formulations although the amount released in any one time across a gradient may vary.

Controlled release formulations in polymeric vehicles have been used for delivery of pesticides, insecticides, fertilizer, detergents, perfumes and in drug delivery. U.S. Pat. No. 5,017,377 to Sikinama et al. discloses a controlled release insect pest repellent used in many settings including p-menthane-3,8-diol blended with an ethylene vinyl acetate copolymer, and is herein incorporated by reference in its entirety.

Controlled release formulations of the present invention can be formulated using either non-degradable or degradable materials. In one type of polymeric delivery system, a polymeric capsule is formed around or incorporating the agent to be delivered. The type of agent being delivered and the environment in which the agent is intended to be used determine the composition of the polymer or polymers used and the method that can be used to incorporate the agent. Alternatively, the polymer can be in the form of a sheet, pellets, a film, or a shaped article.

Examples of controlled release devices and methods are disclosed in "Controlled-Release Delivery Systems for Pesticides" edited by Herbert Scher, 1999 CRC Press.

Timed release formulations of the invention may be prepared in any of several ways. They may be prepared and coated onto, contained within or encapsulated in a physical container, granule, polymer, substrate or barrier which breaks down, corrodes or erodes to release the repellent. When formulated in this manner, the granule, substrate or barrier composition need not be homogeneous in size or content. Hence the time release can be controlled by the size or make-up of the material or materials used as a substrate.

They may also be encapsulated within a coating or chemical layer which, upon contact with water, oxygen, or other environment, chemically reacts to dissolve or degrade the coating or layer thereby releasing the repellent.

Where encapsulation of a repellent formulation is desired, such as where the formulation is to be used in a time release manner or where direct contact with the repellent composition is undesirable, compression within a tablet or cake or containment within a capsule may be employed.

In the tablet/cake embodiment, the tablet formulation may comprise multiple layers comprising a different concentration of formulation in each. Layers may be the same size or vary in size based on the amount of formulation to be released. For example, a binary base formulation, with no additional ingredients may be used in the outer layer or layers for an early concentrated release of repellent while a more dilute formulation having longer release characteristics may be contained deeper within the tablet for extended release effect. In this embodiment, tablets or cakes may be formed in any shape or size suitable to the application. It is well within the skill of one in the agricultural art to form tablets or cakes.

For encapsulation, any number of biodegradable polymers or substrates may be used to surround an effective amount of repellent. The repellent compositions of the present invention may be encapsulated into a matrix by the methods disclosed in U.S. Pat. No. 6,500,463, the contents of which are incorporated herein by reference in their entirety. They may also be incorporated into hydrophobic thermoplastic polymers such as those described in U.S. Pat. No. 6,852,328 to form controlled release matrices. U.S. Pat. No. 6,852,328 is herein incorporated by reference in its entirety.

The repellent compositions of the present invention may also be formulated in hydrogel microbeads each comprising a plurality of active material droplets entrained within a hydrophilic matrix that is cured chemically as disclosed in U.S. Pat. No. 6,793,937, the contents of which are incorporated herein by reference in their entirety.

The repellent compositions of the present invention may be incorporated into inorganic polymer complexes for controlled release as in U.S. Pat. No. 6,391,336; employed in granulation methods alone or as an additive as in the methods of U.S. Pat. Nos. 6,331,193 and 6,299,663; combined with insecticidal proteins such as by the methods disclosed in U.S. Pat. Nos. 6,221,649 and 6,110,463; incorporated into biodegradable plastic products made of coconut mesocarp as disclosed in U.S. Pat. No. 6,083,621; combined with microencapsulated phase change materials such as those described in U.S. Pat. No. 6,057,266 to improve time release; may be incorporated into coated granular pesticide formulations such as those disclosed in U.S. Pat. No. 6,036,971; incorporated into the time release systems described in U.S. Pat. No. 6,004,572; encapsulated in thermoplastic resins such as those described in U.S. Pat. No. 5,679,129; layered into slow release granules such as those in U.S. Pat. No. 4,971,796; or adsorbed in organoclay controlled release formulations such as those disclosed in U.S. Pat. No. 4,849,006, the contents of each patent of which is incorporated herein by reference in its entirety.

Repellent formulations may also be formulated as granular beads or particles for use in post-sale encapsulation by the consumer. In this regard, the repellent formulation may be manufactured such that it may be poured into any fabric or wrapped in a material such as a stocking, sack, sachet, bag, garbage bag and the like. These allow the formulation to be hung or elevated. Alternatively, kits may be provided which include the formulation in combination with a means for application of the time release formulation.

The repellent compositions of the present invention may by applied using global positioning system (GPS) technology as disclosed in U.S. Pat. No. 6,199,000, the contents of which is incorporated by reference herein in its entirety.

The compositions of the present invention may be applied or delivered using osmotic devices such as those described in U.S. Pat. No. 6,491,949, the contents of which are incorporated herein by reference in their entirety.

Controlled delivery of the repellents of the present invention may be to a body of water such as is disclosed in U.S. Pat. Nos. 5,902,596, 5,885,605 and 5,858,384, the contents of each which are incorporated by reference in their entirety.

They may also be formulated for controlled release on land by incorporation into superabsorbent polymers such as those described in U.S. Pat. No. 4,983,390, the contents of which are incorporated by reference in their entirety. Time release may be effected via wicking of the repellent into the atmosphere. As used herein "wicking" is the process by which the repellent composition is moved via capillary action up a tube or along a material. In the present invention, the repellents may be formulated in candles or simply placed in a container with one or more materials used to "wick" the repellent out of the container into the atmosphere. Wicking can be facilitated or non-facilitated. Facilitated wicking occurs via the use of one or more external energy sources such as via the application of heat or use of a fan or both. Non-facilitated wicking occurs naturally in the absence of any applied external energy source, e.g., evaporation.

Time release may be effected by the direct application of heat to either the repellent alone or to the container in which the repellent is placed.

Time released repellent formulations may be placed around or inside buildings, garden areas, vineyards, turf areas, sports fields, parks, campsites, barns, farms, greenhouses, hung on stands or trees and the like. These may also be placed along side roads or other throughways such and walkways and entrances to limit animal entry. They may also be installed on or within vehicles such as under the hood to deter or prevent animal collision.

In one embodiment time release devices include porous bodies or other bodies that can contain a repellent composition and release the composition over time. One such device is a tube with a permeable wall. The tube is filled with a repellent composition such as, but not limited to, a repellent composition of the present invention. The tube is then used to form a boundary. For example, a garden prone to pests may be protected by placing the time release device around the garden. The device may be surface positioned or buried. The effect of the time release device is to deter insects and/or birds.

An exemplary container includes a formulation that comprises a repellent composition of the present invention wherein the container allows for time release of the formulation over a period of one month or more.

Patterned applications are also contemplated. Such applications may be in any shape or may be random. Application may occur in a circular, radial, oval, square, oblong or any other geometric shape necessary to effect coverage of the intended surface, area or substrate. Coverage of the repellent need not be complete or uniform in order to be effective. Coverage levels may be titrated based on the needed repellent effect. For example, coverage may be at the level of at least 10%, at least 20%, at least 30%, at least 40%, at least 50%, at least 60%, at least 70%, at least 80%, at least 90%, at least 95% or 100%.

Repellents and Attractants

The pest management systems of the present invention may be used in combination with the repellents or with attractants known in the art. Attractant formulations of the present invention may comprise of one or a combination of the following natural substances: sugar, honey, molasses, pheromones, plant oils, plant extracts, floral odors, proteins, salt, animal oils such as fish oil and the like, seeds, animal feed, livestock feed, and sticky agents, adhesives including substances such as tanglewood and the like. They may also include commercial pest attractants including poisons. Attractants include compositions and formulations such as those known to those skilled in the art and also disclosed in U.S. Patent Publication Nos. 20100074860 and 20090258950, the contents of which are incorporated herein by reference in their entirety.

As an alternate procedure, the composition can be impregnated into or coated onto a surface to be protected. In this embodiment, a thickener or thixotropic agent is added to the composition.

In another embodiment, the repellent formulations of the present invention may be combined with the urine or one or more animals such as is disclosed in US pre-grant publication number US20100260862 entitled "Time release formulations and methods of making same" the contents of which are incorporated herein by reference in their entirety. The dot delivery apparatus and systems disclosed in US 20100260862 may also be employed using the composition of the present invention.

Both repellent and attractant composition may be applied to or installed in the devices in the form of aerosol, balm, cream, gel, lotion, mousse, patch, pump spray, roll on, solution, gel stick, solid stick, towelette, salve, ointment, powder, liquid, granules, candle, vapor, beads and the like. It is known to those in the art that "towelette" can also be known as a "wet wipe." As an alternate procedure, the composition can be impregnated into crushed eggshells, nutshells or corncobs, wood chips, clay structures (such as clay balls, clay sheets, clay bricks, clay boats, or any other geometric shape), wood based cellulose granules, agglomerized cellulose or other particulate substrates and spread evenly over the area to be protected. For example, in order to produce a sustained release formulation, the repellent compositions of the present invention may act as the "pest control agents" in the compositions disclosed in U.S. Pat. No. 7,846,463, the contents of which are incorporated herein by reference in their entirety.

It should be clear that the particle size of these materials can vary. Particle size may range from dust sized particles to approximately 1 foot in diameter. In one embodiment, particulate substrates are heterogeneous in size and range from the size of a kernel of corn to that of standard wood chips. In one embodiment particulate substrates are from about 1 inch to 10 inches, 1 inch to 5 inches, 1 inch to 3 inches, or approximately 2 inches. Typically 1 to 10, 1 to 5, or 1 to 3 ounces of concentrated formula is used to wet 1 pound of granular or particulate material. In another embodiment, the particulate substrates may be soaked in either a concentrated formula or one which has been diluted according to the invention. Once dry, the 1 pound of granular or particulate product can be applied to 1000 square feet of surface area. Depending on the desired coverage, more than one application may be made.

In another embodiment, the composition can be left in containers which are distributed in a uniform manner around the area being treated.

Various types of solid materials may be protected by the disclosed repellent compositions. Plant material, including woody plants may be protected from browsing animals. Plant material including grasses, may be sprayed to prevent insects from alighting on the plant. Seed, including bird, vegetable, flower, plant, may be protected from wandering animals such as rodents, by mixing the repellent of the present invention with the seed to be protected.

Exterior surfaces of buildings, walls, concrete and asphalt and other solid non-living surfaces may be sprayed to prevent animals from alighting on, approaching or otherwise contacting such surfaces.

The repellent formulations may be applied to clothing or other fabric or sheet goods to prevent insects from alighting on the material or biting through the material. The fabric may be permeable or impermeable and may be woven or non-woven. Examples of materials to which the compositions may be applied are cottons and other natural fibers or synthetic fibers or sheet goods such as nylon, polyester or polypropylene. If the material is permeable the composition may be absorbed; if impermeable the composition will act as a coating on the surface of the fiber or sheet goods. In one embodiment, the repellent compositions may be mixed in a paper slurry and pressed into paper sheets such as napkins or tablecloths for outdoor use to deter insects. Paper products made in this way may be used to wrap around plants (stems, trunks or other parts) or cover physical structures to deter pest ingress or egress. They may also be mixed in screen printing fluids and printed onto articles of manufacture such as shirts or any fabric amenable to screen printing.

The formulations may be applied to articles of adornment such as jewelry or bands such as wrist bands, hats, caps or any head covering, covering for the hands such as gloves or mittens, as well as shoes, boots, waders, suspenders and the like. They may also be incorporated into systems having butane heated cartridges such as those designed to emit odors to ward off pests. The formulations of the present invention may be used in personalized pest repellent devices such as those worn around the neck, wrist, waist or ankle or those attached to clothing. The personalized pest repellent devices may be motorized or they may be passively activated. The motorized devices may depend on battery or solar power to run the devices. The personalized pest repellent devices may attach to a belt, hat, suspenders, backpack, purse, bag, pocket, shoe, boot, pants, shirt or jacket, or hang around the neck, waist, shoulder, or wrist.

The formulations may be applied to or mixed into candles. These candles may be citronella candles or decorative candles. The wax of the candle may be selected from the group consisting of but not limited to carnauba wax, candelilla wax, beeswax, synthetic wax, shellac wax, spermaceti, lanolin wax, ozokerite, bran wax, ceresin wax, bayberry wax, paraffin, rice wax, jojoba wax, soy wax, palm wax, candle gel and a combination thereof.

In one embodiment, the formulation may be applied to the skin, fur or pelt of pets and domestic or other animals such as, but not limited to, livestock in order to minimize insect problems. The formulation may be applied directly to the animal's coat or pelt by spraying, pouring or massaging the liquid formulation into the coat or pelt. Emulsions of polymers comprising the repellents of the present invention may also be used on the skin of animals as described in U.S. Pat. No. 4,783,335 the contents of which are incorporated herein by reference in their entirety. Pet accessories or adornments such as clothing, leashes, tags, or collars may also be treated with the formulations of the invention. Use of the composition on the surface of various farm structures, particularly on surfaces inside barns where animals are kept or milked will minimize insect interference with farm operations and animals. Livestock accessories or adornments such as harnesses, ear tags, saddles, reins, or blankets may also be treated with the formulations of the invention. The repellent compositions of the present invention may be used to improve cultivation methods and employed in methods such as those described in U.S. Pat. No. 6,887,828, the contents of which are incorporated herein by reference in their entirety.

In one embodiment, the formulation may be applied to the skin, fur or pelt of pets and domestic or other animals such as, but not limited to, livestock in order to repel predators. The formulation may be applied directly to the animal's coat or pelt by spraying, pouring or massaging the liquid formulation into the coat or pelt. Emulsions of polymers comprising the repellents of the present invention may also be used on the skin of animals as described in U.S. Pat. No. 4,783,335 the contents of which are incorporated herein by reference in their entirety. Pet accessories or adornments such as clothing, leashes, tags, or collars may also be treated with the formulations of the invention. Use of the composition on the surface of various farm structures, particularly on surfaces inside barns where animals are kept or milked may minimize the appearance of predators and the interference with farm operations and animals. Livestock accessories or adornments such as harnesses, ear tags, saddles, reins, or blankets may also be treated with the formulations of the invention. Further, the repellent formulations described herein may be applied to barns, pastures, grazing areas, stables, animal feed, feeding apparatus, fencing and/or other animal containment apparatus, shrubs, trees, ground cover such as, but not limited to, rocks, grass, crops, brush, dirt and soil, and other manmade apparatus and/or devices which may be near livestock.

The formulation may also be applied to the skin of humans, preferably by spraying or in the form of a gel, cream or lotion. The spray may be in aerosol form or may be pump-spray form.

In one embodiment the repellent compositions of the present invention are transparent.

Equivalents and Scope

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

EXAMPLES

The following examples are given for purposes of illustration and not by way of limitation. Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below. The present invention is illustrated further by the following non-limiting Examples.

Example 1

Repellent Formulations for Outdoor Use

An animal repellent concentrate for outdoor application is made by mixing one of the described concentrate of formulations A-M of Tables 6 and 7 with water as follows:

When added to water in the ratio of one (1) part concentrate with one and a half (1.5) parts water and sprayed onto hard surfaces, either indoor or outdoor, including garbage receptacles, the formulation is useful to repel large animals. Such animals include those traditionally found outside such as dogs, cats, deer, bears, rodents and the like.

Depending on the desired coverage, the above formulation may be as dilute as one (1) part concentrate with up to twenty (20) parts diluents (preferably water).

Example 2

Application to Hard Surfaces

An animal repellent concentrate selected from formulations A-M of Tables 6 and 7 is added to water at the ratio of one (1) part concentrate with nine (9) parts water and applied to hard surfaces and grass areas will repel Canadian geese and blackbirds from surfaces treated. One (1) gallon of this diluted mixture will treat a one (1) acre area. This mix will also kill aphids, caterpillars, and the like.

Example 3

Applications to Plants

When added to water at the ratio of one (1) part concentrate of a repellent formulation selected from formulations A-M of Tables 6 and 7 to nineteen (19) parts water and applied to plant foliage, the formulations will repel such animals as deer, rabbit, and the like from feeding on them. This can also be sprayed onto a ribbon and placed thirty (30) inches above ground around plants to keep deer from entering the area and eating plants. In this embodiment, one preferred ribbon would be ¾ inches wide and made of any suitable material and length necessary.

Example 4

Thickening

To increase the concentration or amount of repellent applied in a defined area, or to control specific applications a formulation having a thicker consistency may be necessary. Thicker formulations may be prepared by the addition of xanthan gum. For example, a quantity of repellent formulation selected from formulations A-M of Tables 6 and 7 (in concentrated or diluted form) may be mixed with approximately 0.5 ounce xanthan gum as a thickener.

Example 5

Adherence Modifications

To increase adherence, a repellent formulation selected from formulations A-M of Tables 6 and 7 (in concentrated or diluted form) is mixed with approximately 2 ounces of kaolin clay powder per gallon of concentrate formulation, to act as a sticker, to aid in the adherence of the formulation to the surface to be treated.

Example 6

Admixtures with Eggshells

A solid formulation of the animal repellent is formed by admixing 1 pound of crushed eggshells with about 1.25 fluid ounces of the animal repellent formulation selected from formulations A-M of Tables 6 and 7 (in concentrated or diluted form), drying the repellant particle and evenly distributing the repellant over the area to be protected.

Example 7

Admixtures with Granular Material

A solid formulation of the animal repellent formulation is formed by admixing about 1 pound of granular or particulate material such as corncobs with about 1.25 fluid ounces of the animal repellent formulation selected from formulations A-M of Tables 6 and 7 (in concentrated or diluted form) and drying the repellant particle and evenly distributing the repellant over the area to be protected.

Example 8

Admixtures with Nutshells

A solid formulation of the animal repellent formulation is formed by admixing about 1 pound of crushed nutshells with about 1.25 fluid ounces of the animal repellent formulation selected from formulations A-M of Tables 6 and 7 (in concentrated or diluted form), drying the repellant particle and evenly distributing the repellant over the area to be protected.

Example 9

Repellent-Coated Particulates

A solid formulation of the repellent formulation selected from formulations A-M of Tables 6 and 7 is prepared by mixing about one pound by weight of crushed eggshells, nutshells, or corncobs granules in a particle size distribution from dustless fine particles to about one-quarter inch overall thickness particles with about 3 fluid ounces of the selected animal repellent formulation (in concentrated or diluted form), drying the repellant particles and evenly distributing the repellant-coated over the area to be protected.

The formulation can also be applied onto a ribbon of any type and size and placed around areas to be protected. For example, it may be applied to a string or rope and hung from any elevation, for example from a tree. One or more coated strips or ribbons may be hung from any one elevated structure.

Example 10

Freeze-Dried Repellent Formulation

An animal or insect repellent may be prepared by coating about 4 ounces of repellent formulation selected from formulations A-M of Tables 6 and 7 onto about one pound weight of straw, hay, seeds, grains, ground corncob, mulch, wood particles and/or compressed wood, and the mixture is then freeze-dried.

Example 11

Personal Repellent Apparatus for Humans

An animal or insect repellent to be worn by humans may be prepared where the about one ounce of the liquid repellent formulation selected from the formulations A-M of Tables 6 and 7 is coated onto an inch-square polymer, cloth, or paper and stored in an apparatus which may attach to clothing, fabric or a person. For example the apparatus can attach to a belt, hat, suspenders, backpack, purse, bag, pocket, shoe, boot, pants, shirt, and/or jacket, or hang around the neck, waist, shoulder or wrist.

Example 12

Candle Repellent Formulation

A candle of the animal or insect repellent formulation may be prepared by mixing about three ounces of the repellent formulation selected from the formulations A-M of Tables 6 and 7 and about two ounces of citronella into about a half of a pound of melted soy wax, pouring the wax around a wick, and allowing the wax mixture to dry creating a candle. The candle may be lit so the flame melt the wax and disperse the formulation into the air. The formulation may also be released by using a warming plate to melt the wax and disperse the formulation into the air.

Example 13

Gel Repellent Formulation

A gel of the animal or insect repellent formulation may be prepared by mixing about four ounces of the repellent formulation selected from the formulations A-M of Tables 6 and 7 and about two ounces of citronella into about a quarter of a pound of liquid gel wax and the mixture is poured into a mold to solidify after which the solidified mixture may be exposed to air to disperse the formulation.

Example 14

Repellent Formulation for Pets

A liquid formulation of the repellent formulation selected from the formulations A-M of Tables 6 and 7 may be prepared by mixing about two ounces of solvent with about one ounce of the selected repellent formulation. The formulation may be used to coat pet collars, tags, or pet clothing which is then attached to the pet or the liquid formulation may be applied directly to the pets coat by spraying, pouring or massaging the liquid formulation into the coat.

Example 15

Liquid Geraniol Repellent Formulation for Deterring Predators

A liquid formulation of a repellent formulation containing geraniol as described herein may be prepared by mixing four ounces of solvent, preferably water, with about three ounces of the repellent formulation. The formulation may be used to coat harnesses, ear tags, saddles, reins, blankets, clothing, leashes, tags, or collars which may be used by animals including, but not limited to, pets and livestock. The liquid formulation may also be applied directly to an animal's pelt, fur and/or coat by spraying, pouring or massaging the liquid formulation into the coat or pelt.

Example 16

Liquid Repellent Formulation for Livestock

A liquid formulation of the repellent formulation selected from the formulations A-M of Tables 6 and 7 may be prepared by mixing about four ounces of solvent, preferably water, with about three ounces of the selected repellent formulation. The formulation may be used to coat harnesses, ear tags, saddles, reins or blankets which may be used on the livestock. The liquid formulation may also be applied directly to the livestock pelt, fur and/or coat by spraying, pouring or massaging the liquid formulation into the coat or pelt.

Example 17

Solid Geraniol Repellent Formulation for Deterring Predators

A solid formulation of a repellent formulation containing geraniol may be prepared by mixing about one pound of crushed eggshells, nutshells, or corncob granules in a particle size distribution from dustless fine particles to about one-quarter inch overall thickness particles with about 3 fluid ounces of the repellent formulation containing geraniol, drying the repellent particles and distributing the repellent particles. The repellent particles may be distributed in barns, stables, pens, grazing areas, lawns, yards, fields, pastures, or other areas where animals such as, but not limited to, pets and livestock, may gather and may also be distributed onto an animal's pelt, fur and/or coat.

Example 18

Solid Repellent Formulation for Livestock

A solid formulation of the repellent formulation selected from the formulations A-M of Tables 6 and 7 may be prepared by mixing about one pound of crushed eggshells, nutshells, or corncob granules in a particle size distribution from dustless fine particles to about one-quarter inch overall thickness particles with about 3 fluid ounces of the animal repellent formulation A, B, C or D, drying the repellent particles and distributing the repellent particles in barns, stables, pens, grazing areas, pastures, or other areas where livestock may gather.

Example 19

Aerial Application Formulation

A liquid formulation of the repellent formulation selected from the formulations A-M of Tables 6 and 7 may be prepared by mixing about 25 gallons of the selected repellent formulation with about 40 gallons of solvent.

Example 20

Seed Application Formulation

A solid formulation of the repellent formulation selected from the formulations A-M of Tables 6 and 7 may be prepared by mixing 10 grams of the selected repellent formulation with about 1 pound of seed.

Example 21

Fertilizer Application Formulation

A solid formulation of the repellent formulation selected from the formulations A-M of Tables 6 and 7 may be prepared by mixing 10 grams of the selected repellent formulation for each pound of fertilizer.

Example 22

Formulation for Controlled Release

An animal repellent concentrate for controlled release is made by mixing the described concentrate of a repellent formulation selected from the formulations A-M of Tables 6 and 7 with water as follows:

When added to water in the ratio of one (1) part concentrate with one and a half (1.5) parts water and stored in vials with small holes allowing for the repellent formulation to emit through.

Example 23

Liquid Spray Formulation

A liquid formulation of a repellent formulation selected from formulations A-M of Tables 6 and 7 may be prepared by mixing about 1 gallon of repellent formulation with about 5 to 20 gallons of water. The liquid formulation may then be sprayed on hard surfaces or plants to prevent the ingress of animals, such as house pets or deer, into the sprayed area.

Example 24

Mole Repellent Formulation

A liquid formulation of a repellent formulation selected from formulations A-D or F of Table 6 may be prepared by mixing about 1 gallon of repellent formulation with about 5 to 20 gallons of water. The liquid formulation may then be sprayed on hard surfaces or plants to prevent the ingress of moles.

A solid formulation of the repellent formulation selected from formulations A-D or F of Table 6 is prepared by mixing about one pound by weight of crushed eggshells, nutshells, or corncobs granules in a particle size distribution from dustless fine particles to about one-quarter inch overall thickness particles with about 3 fluid ounces of the selected animal repellent formulation (in concentrated or diluted form), drying the repellant particles and evenly distributing the repellant-coated over the area to be protected. The particles may then be spread on lawns or other surfaces to prevent the ingress of moles.

Example 25

Snake Repellent Formulation

A liquid formulation of a repellent formulation selected from formulations G or F of Tables 6 and 7 may be prepared by mixing about 1 gallon of repellent formulation with about 5 to 20 gallons of water. The liquid formulation may then be sprayed on hard surfaces or plants to prevent the ingress of snakes.

Example 26

Vapor Repellent Formulation

A liquid formulation of a repellent formulation selected from formulations A-M of Tables 6 and 7 may be prepared by mixing about 1 gallon of repellent formulation with about 5 to 20 gallons of water. The liquid formulation may then be saturated on an absorbent material. Hot directed air may then be directed over the absorbent material in crawl spaces, containers, cargo spaces and other areas where pests prefer to hide.

Example 27

Repellent Seed Composition

Formulation Q, described previously, is combined with seeds in the amount of 10 g of Formulation Q per pound of seeds to produce a repellent seed composition. Treated seeds are resistant to consumption and destruction by birds, rodents and insects.

Example 28

Rodent Repellent Assay

In a warehouse situation, a repellent seed composition was prepared by treating birdseed with Formulation Q (10 g of Formulation Q/pound of seed) and then used as bait. Treated seeds were placed in a dish and a light film of fine sand was spread around the dish for a distance of 3 to 4 inches around the dish. The sand around the dish was used to detect mouse visitation to the baited seed in the dish. In the following mornings, the test site was visited to see if there was any mouse or rat activity in the test dish and sand preparation. The test site was replicated 6 times including a control site with a dish of seeds that were not treated. Although all test sites were visited by mice (as shown by their footprints in the sand), none of the test dishes with treated seeds had noticeable seed missing, whereas the untreated seeds in the control site were totally missing. Test site inspection continued every morning for about 2 weeks showing little or no treated seed missing. Although mice visited the treated seed, surprisingly, they were highly repelled by the seed treatment.

Example 29

Granular Repellent Composition

A granular repellent composition is prepared. Formulation C3, described previously, is combined with crushed walnut shells in the amount of 19.5 g of Formulation C3 per pound of crushed walnut shells. The treated material is allowed to dry. The treated walnut shells are used to repel rodents and other pests.

Example 29

Groundhog Repellent Assay

In a natural field situation, a groundhog hole (e.g. borough) was found and sealed with soil to verify that the hole was actively used. If the soil was removed within 24 hours, then the hole or entry was an "active site" being used by the groundhog. In active sites, 8 ounces of a granular repellent composition (comprising crushed walnut shells treated with the concentrated formulation of C3 at a ratio of 19.5 g of C3 per pound of crushed walnut shells) was thrown into the hole and covered with soil. An additional 8 ounces of treated material was spread around the entry hole. This was replicated in 2 other holes that were found in the area. After 14 days had passed, only one of the 3 entries was breached by the groundhog. It was retreated and no further entry into any of the holes was observed for the remainder of the summer.

The invention claimed is:

1. A method of preparing a repellent seed composition comprising:
   a. Preparing a repellent formulation comprising 5.0 to 7.5 weight percent of geraniol oil; 2.0 to 5.0 weight percent of castor oil; 6.0 to 9.0 weight percent of peppermint oil; 2.0 to 8.0 weight percent of rosemary oil; 4.0 to 8.0 weight percent of cinnamon oil; 0.1 to 0.5 weight percent of xanthan gum; 0.9 to 2.0 weight percent of kaolin clay; and 60 to 80 weight percent of water; and
   b. Treating seeds by combining said repellent formulation with said seeds at a ratio of about 10 g of repellent formulation per 1 pound of seeds.

2. The method of claim 1, wherein the treated seeds are further allowed to dry.

3. The method of claim 2, wherein said repellent formulation comprises:
   a. 5.5 weight percent of geraniol oil;
   b. 2.5 weight percent of castor oil;
   c. 6.6 weight percent of peppermint oil;
   d. 4.5 weight percent of rosemary oil;
   e. 4.9 weight percent of cinnamon oil;
   f. 0.15 weight percent of xanthan gum;
   g. 1.1 weight percent of kaolin clay; and
   h. 74.75 weight percent of water.

4. A repellent seed composition produced according to the method of claim 3.

5. A method of reducing or eliminating seed consumption by pests comprising the use of the repellent seed composition of claim 4.

6. The method of claim 5, wherein seed consumption by pests is reduced or eliminated for a period of from about 5 weeks to about 50 weeks.

7. The method of claim 5, wherein seed consumption by pests is reduced or eliminated for a period of from about 2 weeks to about 10 weeks.

8. The method of claim 5, wherein said repellent seed composition comprises grass seeds.

9. A method of storing seeds comprising:
   a. preparing a repellent seed composition by combining seeds with a repellent formulation at a ratio of 10 g of repellent formulation per pound of seed, wherein said repellent formulation comprises 5.5 weight percent of geraniol oil; 2.5 weight percent of castor oil; 6.6 weight percent of peppermint oil; 4.5 weight percent of rosemary oil; 4.9 weight percent of cinnamon oil; 0.15 weight percent of xanthan gum; 1.1 weight percent of kaolin clay; and 74.75 weight percent of water;
  b. allowing the repellent seed composition to dry; and storing the repellent seed composition.

10. A method of preparing a granular repellent composition comprising:
  a. preparing a concentrated repellent formulation comprising 0.05 to 30 weight percent of geraniol oil; 0.2 to 55 weight percent of castor oil; 10 to 25 weight percent of peppermint oil; 15 to 25 weight percent of rosemary oil; 5 to 20 weight percent of cinnamon oil; 0.01 to 5 weight percent of xanthan gum; 0.01 to 5 weight percent of kaolin clay; and 0 to 69.73 weight percent of water; and
  b. Treating a granular material by combining said concentrated repellent formulation with said granular material at a ratio of about 10 g of concentrated repellent formulation per 1 pound of granular material to about 30 g of the concentrated repellent formulation per 1 pound of granular material.

11. The method of claim 10, wherein the treated granular material is further allowed to dry.

12. The method of claim 11, wherein said concentrated repellent formulation comprises:
  a. 5.75 weight percent of geraniol oil;
  b. 20 weight percent of castor oil;
  c. 16.49 weight percent of peppermint oil;
  d. 21.57 weight percent of rosemary oil;
  e. 10.8 weight percent of cinnamon oil;
  f. 0.23 weight percent of xanthan gum;
  g. 1.1 weight percent of kaolin clay; and
  h. 24.06 weight percent of water.

13. The method of claim 12, wherein said granular material comprises crushed walnut shells.

14. A granular repellent composition produced according to the method of claim 13.

15. A method of repelling pests from an area comprising the use of the granular repellent composition of claim 14.

16. The method of claim 15, wherein said pest is a rodent selected from the group consisting of mice, rabbits, squirrels, and groundhogs.

17. The method of claim 16, wherein said pest is a groundhog and wherein said area comprises a groundhog borough.

18. The method of claim 17, wherein said granular repellent composition is applied inside and around said groundhog borough.

19. The method of claim 18, wherein said granular repellent composition is applied at least twice.

* * * * *